United States Patent [19]

Floyd, Jr.

[11] 4,298,754
[45] Nov. 3, 1981

[54] 15-DEOXY-16-HYDROXY-16-(1′FLUOROVINYL) PROSTAGLANDINS AND DERIVATIVES

[75] Inventor: Middleton B. Floyd, Jr., Suffern, N.Y.

[73] Assignee: American Cyanamid Company, Stamford, Conn.

[21] Appl. No.: 46,726

[22] Filed: Jun. 7, 1979

[51] Int. Cl.³ ............................................. C07C 177/00
[52] U.S. Cl. .................................. 560/121; 260/408; 260/438.1; 562/503; 424/305; 424/318
[58] Field of Search ......................... 560/121; 562/503; 260/408

[56] References Cited

U.S. PATENT DOCUMENTS 4,191,699  3/1980  Floyd ........................... 260/448.2 D Primary Examiner—Robert Gerstl
Attorney, Agent, or Firm—Richard J. Hammond

[57] ABSTRACT

15-Deoxy-16-hydroxy-16-(1 halovinyl) prostaglandins have been prepared.

20 Claims, No Drawings

15-DEOXY-16-HYDROXY-16-(1'FLUOROVINYL) PROSTAGLANDINS AND DERIVATIVES

BACKGROUND OF THE INVENTION (1) Field of the Invention

The present invention relates to 15-deoxy-16-hydroxy-16-(1'fluorovinyl),-16-(1'-chlorovinyl) and 16-(1'bromovinyl) prostaglandins, as well as the pharmaceutically acceptable, non-toxic lower alkyl esters and salts thereof, and to the intermediates and processes for producing such compounds.

(2) Description of The Prior Art

Prostaglandins have classically been described as chemically related 20 carbon chain hydroxy fatty acids having the basic skeleton of prostanoic acid:

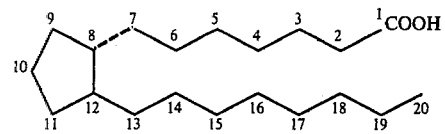

The prostaglandins having a hydroxyl group at the C-11 position and a keto group at the C-9 position are known as the PGE series, and those having a hydroxyl group in place of the keto group are known as the PGF series and are further designed by an α or β suffix to indicate the configuration of the hydroxyl group at said position. The natural compounds are the α-hydroxy substituted compounds. They may contain different degrees of unsaturation in the molecule, particularly at C-5, C-13 and C-17, the unsaturation is also indicated by a suffix. Thus, for example, the $PGF_1$ and $PGE_1$ series refer to prostanoic acids having a trans olefin bond at the C-13 position, while the $PGF_2$ and $PGE_2$ series refer to prostadienoic acids having a cis-olefin bond at the C-5 position and a trans olefin bond at the C-13 position. For a review on prostaglandins and the definition of primary prostaglandins, see, for example, P. Ramwell, *The Prostaglandins*, 1, pp. 5-22 (1973).

The preparation of derivatives of prostanoic acid has become of great importance since the demonstration of the highly interesting range of biological and pharmacological activities of natural prostaglandins.

The great majority of these studies have focused on modification of the two side chains, or modifications of the substituents attached to the cyclopentane moiety [see for example U. Axen et al., *Synthesis* Vol. 1, John Wiley and Sons Inc., New York, N.Y. 1973 and P. H. Bentley, *Chem. Soc. Reviews* 2, 29 (1973)].

The synthesis of prostaglandin analogs possessing a 3-oxa- or 11-deoxy-3-thia moiety have been described, among others in U.S. Pat. No. 3,873,607; U.S. Pat. No. 3,950,406; Netherlands Patent 7305222-Q; U.S. Pat. No. 3,944,593; U.S. Pat. No. 3,931,289; and U.S. Pat. No. 3,936,487.

The synthesis of several prostaglandin analogs wherein the hydroxyl group at C-15 has been removed and a hydroxyl group has been introduced at C-16 has appeared [see for example, U.S. Pat. No. 3,950,406; *Prostaglandins*, Vol. 10, 733 (1975); *Tetrahedron Letters*, No. 48, 4217 (1975)].

Recently reports have also appeared wherein the C-16 carbon bearing a hydroxyl group is substituted with a methyl group [see Pappo et al., *Tetrahedron Letters*, No. 4, 235 (1975); Collin et al., U.S. Pat. No. 3,965,143; and Belgium Pat. No. 827,127].

Also, a patent has recently appeared wherein the C-16 carbon bearing the hydroxyl group is substituted with vinyl, methylvinyl, and cyclopropyl (U.S. Pat. No. 4,061,670), and U.S. Pat. No. 4,132,738 disclosing 15-deoxy 16-hydroxy 16-alkyl PGE, carbinols.

SUMMARY OF THE PRESENT INVENTION

In accordance with the present invention, we have prepared certain novel 15-deoxy-16-hydroxy-16-halovinyl prostaglandin analogs represented by the following formula:

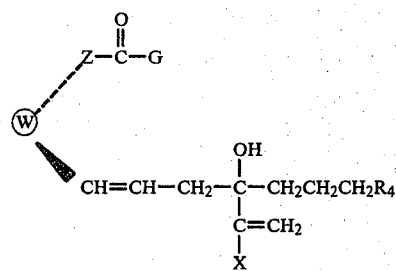

or a racemic mixture thereof and the mirror image thereof wherein W is selected from the group

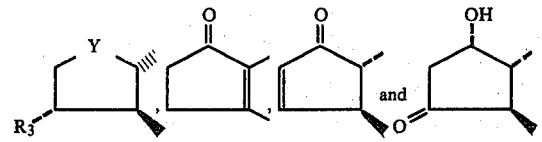

or wherein Y is a divalent moiety selected from

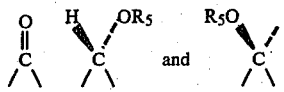

wherein $R_5$ is hydrogen or $C_2$ to $C_6$ alkanoyl;
$R_3$ is selected from the group hydrogen and hydroxy;
$R_4$ is selected from the group hydrogen and $C_1$ to $C_3$ alkyl; G is selected from the group hydroxy, $-OR_1$, wherein $R_1$ is selected from the group hydrogen, $C_1$ to $C_6$ alkyl, phenyl and substituted phenyl; Z is selected from the group

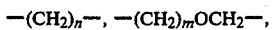
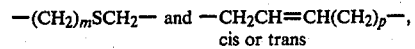

wherein n is the integer 5 to 8, m is the integer 3 to 6 and p is the integer 2 to 5; and X is selected from the group fluorine, chlorine and bromine and when G is hydroxy, the pharmaceutically acceptable salts thereof.

The dotted lines shown in the above formula and in the formulas below indicate that the substituents are in α configuration, i.e., below the plane of the cyclopentane ring.

The double bond at C-13 in the compounds of the present invention has the same configuration as in natural prostaglandins of the PGE and PGF series, that is the trans configuration.

These novel compounds possess asymmetric centers and thus can be produced as racemic mixtures or as individual enantiomers. The racemic mixtures can be resolved if desired at appropriate stages by methods known to those skilled in the art, to obtain the respective individual enantiomers. It is to be understood that the racemic mixtures and the individual 8R-enantiomers are encompassed within the scope of the present invention.

When the compounds of the present invention are racemic mixtures, they are produced starting from racemates, while when the compounds of the invention are individual enantiomers the compounds are preferably obtained starting from the appropriate individual enantiomer.

Useful pharmacologically acceptable salts of the above formula, where $R_1$ is hydrogen, are those with pharmacologically acceptable metal cations, ammonium, amine cations or quaternary ammonium cations.

Preferred metal cations are those derived from the alkali metals, e.g. lithium, sodium and potassium, and from the alkaline earth metals, e.g. magnesium and calcium, although cationic forms of other metals, e.g. aluminum, zinc and iron, are within the scope of this invention.

Pharmacologically acceptable amine cations are those derived from primary, secondary or tertiary amines such as mono-, di- or trimethylamine, ethylamine, dibutylamine, triisopropylamine, N-methylhexylamine, decylamine, dodecylamine, allylamine, crotylamine, cyclopentylamine, dicyclohexylamine, mono- or dibenzylamine, α- or β-phenylethylamine, ethylenediamine, diethylenetriamine, and aryliphatic amines containing up to and including 18 carbon atoms, as well as heterocyclic amines, e.g. piperidine, morpholine, pyrrolidine, piperazine and lower alkyl derivatives thereof, e.g. 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g. mono-, di-, or triethanolamine, ethyldiethanolamine, N-butylethanolamine, 2-amino-1-butanol, 2-amino-2-ethyl-1,3-propanediol, 2-amino-2-methyl-1-propanol, tris(hydroxy-methyl)aminomethane, N-phenylethanolamine, N-(p-tert-amylphenyl(diethanolamine, galactamine, N-methylglucamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium and the like.

DESCRIPTION OF THE PREFERRED EMBODIMENTS

Compounds of the formula

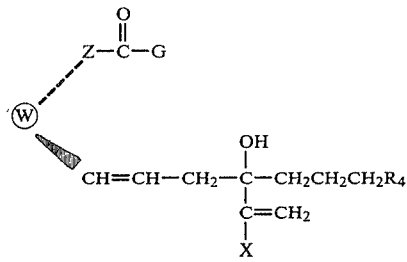

or a racemic mixture thereof and the mirror image thereof wherein W is selected from the group

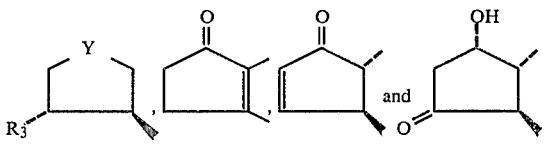

wherein Y is a divalent moiety selected from

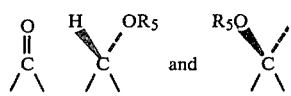

wherein $R_5$ is hydrogen or $C_2$ to $C_6$ alkanoyl;

$R_3$ is selected from the group hydrogen and hydroxy; $R_4$ is selected from the group hydrogen and $C_1$ to $C_3$ alkyl; G is selected from the group hydroxy, $-OR_1$, wherein $R_1$ is selected from the group hydrogen, $C_1$ to $C_6$ alkyl, phenyl and substituted phenyl; Z is selected from the group $-(CH_2)_n-$, $-(CH_2)_mOCH_2-$, $-(CH_2)_mSCH_2-$ and $-CH_2CH=CH(CH_2)_p-$, cis or trans wherein n is the integer 5 to 8, m is the integer 3 to 6 and p is the integer 2 to 5; and X is selected from the group fluorine, chlorine and bromine and when G is hydroxy, the pharmaceutically acceptable salts thereof.

Subgenerically the compounds of the present invention are of the following formula:

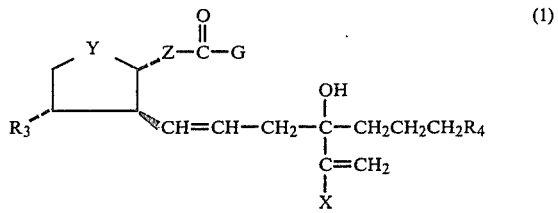 (1)

wherein Y is a divalent moiety selected from

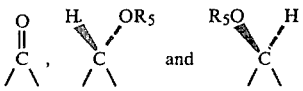

wherein X, G, Z, $R_3$, $R_4$ and $R_5$ are as previously described. In these compounds, it is preferred that $R_5$ is hydrogen; G is selected from the group hydroxy and —OR$_1$ wherein R$_1$ is selected from the group hydrogen and C$_1$ to C$_6$ alkyl; Z is selected from the group

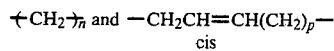

wherein n is the integer 5 to 8 and p is the integer 2 to 5; X is fluorine and R$_5$, R$_4$ are as previously defined. In these preferred compounds, where Y is the divalent moiety

it is most preferred that R$_3$ is hydroxy and R$_4$ is C$_1$ alkyl.

Where Y is the divalent moiety.

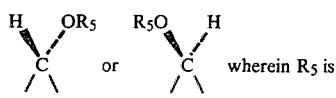

wherein R$_5$ is hydrogen on the preferred compounds, it is most preferred that R$_3$ is hydroxy and R$_4$ is C$_1$ alkyl.

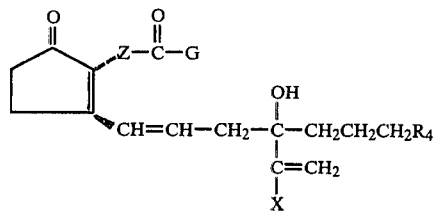

(2)

wherein Z, G, X and R$_4$ are as previously defined. In these compounds, it is preferred that G is selected from the group hydroxy and —OR$_1$ wherein R$_1$ is selected from the group hydroxy and C$_1$ to C$_6$ alkyl; Z is selected from the group

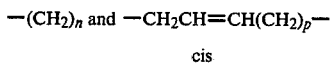

wherein n is the integer 5 to 8 and p is the integer 2 to 5; X is fluorine, R$_4$ is as previously defined. In these preferred compounds it is most preferred that R$_4$ is C$_1$ alkyl.

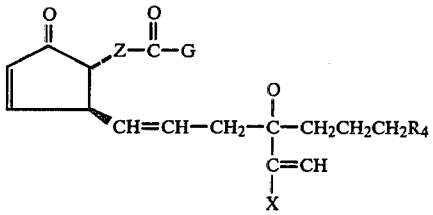

(3)

wherein Z, 6, and R$_4$ are as previously defined. In these compounds, it is preferred that G is selected from the group hydroxy and —OR$_1$ wherein R$_1$ is selected from the group hydrogen and C$_1$ to C$_6$ alkyl; Z is selected from the group

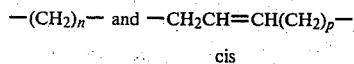

wherein n is the integer 5 to 8 and p is the integer 2 to 5; X is fluorine and R$_4$ is as previously defined. In these preferred compounds, it is most preferred that R$_4$ is C$_1$ alkyl.

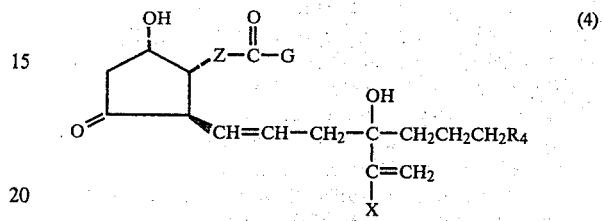

(4)

wherein Z, G, X and R$_4$ are as previously defined. In these compounds, it is preferred that G is selected from the group hydroxy and —OR$_1$ wherein R$_1$ is selected from the group hydrogen and C$_1$ to C$_6$ alkyl; Z is selected from the group

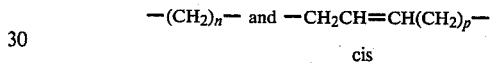

wherein n is the integer 5 to 8 and p is the integer 2 to 5; X is fluorine and R$_4$ is as previously defined. In these preferred compounds, it is most preferred that R$_4$ is C$_1$ alkyl.

The novel compounds of this invention can be prepared by 1,4-conjugate-addition procedure involving treatment of an ether blocked cyclopentenone with a lithio-cuprate reagent prepared as illustrated in Flowsheets A, B, C and D.

The preparation of the precursor compounds that ultimately result in the 16-hydroxy-16-(1-halovinyl) prostanes is schematically shown in Flowsheet A. As the initial step, a vinyl alkoxide is treated with bromine (or chlorine) in the classical manner thereby adding the halogen to the double bond and forming the 1,2-dibromide (step 1). Any linear or branched C$_5$ to C$_8$ alkyl Grignard reagent displaces the halide at the 2-carbon position to form a 1-bromo (or chloro)-2-alkoxyalkane. Shown in the flowsheet, is the function of the compound 1-bromo-2-alkoxyhexane (step 2). The above reaction is preferably carried out in ether solution at temperatures below 0° C., typically −15° for from about 1 hour to about 48 hours. The compound of step 2 is then dehydrohaloginated preferably with an alkali or alkaline earth metal hydride in an aprotic solvent to yield a 2-alkyl-2-alkoxy-1-ethene (step 3). Temperatures and times of reaction are selected to maximize yields as much as possible and are usually from about 60°–100° for 10 minutes to 24 hours. The product of step 3 is cyclized, simultaneously adding the fluorochloromethylenic moiety to the cyclized product by a base catalyzed condensation with dichlorofluoromethane in the presence of a crown ether (preferably 18-crown-6-ether) catalyst. The cyclized product, a 2-alkyl-1-chloro-2-alkoxy-1-fluorocyclopropane (step 4), illustrated as a 1-chloro-1-fluoro-2-butyl-2-alkoxycyclopropane is formed after about 15 minutes to 24 hours at temperatures typically below room temperature, i.e., from about −25° to about 10°. Other halogen adducts of the cyclopropane of step 4 can also be formed by using, in place of the dichlorofluoromethane, dichlorobromomethane or trichloromethane. Ring opening of the cycled product is preferably effected by a base-catalyzed solvolytic reaction in ethanol at elevated temperatures, typically 60°–100° using an alkali or alkaline earth carbonate or bicarbonate i.e., potassium carbonate, providing the intermediate of step 5 which is subsequently hydrolyzed to the desired 2-fluoro-1-alken-5-one by treatment with dilute mineral acid in a protic inert solvent, e.g., tetrahydrofuran (step 6). By the procedure of U.S. Pat. No. 4,061,670, incorporated herein by reference, a Grignard reaction of the ketone of step 6 with propargyl magnesium bromide provides the 4-hydroxy-4-(1')-fluorovinyl)-1-octyne (step 7). As noted earlier and reiterated here, the length of the alkylynyl chain can be adjusted in the desired range by varying the alkyl moeity of the Grignard reagent of step 2. Thus, instead of the 1-octyne illustrated by step 7, it is possible to form the 1-heptyne or 1-nonyne analogs simply by using n-propyl magnesium bromide or n-pentyl magnesium bromide respectively in place of n-butyl magnesium bromide in step 2. Protection of the free hydroxyl group is accomplished in the usual manner using preferably, trimethylsilylchloride. See U.S. Pat. No. 4,061,670 (Step 8 where TMS is trimethylsilyl). Formation of the vinyl lithium request (the product of step 10) can be accomplished by procedures known in the prior art. Thus, the reaction of trimethylsilyloxy derivative of step 8 with a trialkylstannane, e.g., tri-n-butyl-stannane in the presence of a free radical source such as azobisisobutyronitrile provides the vinylstannane (step 9), which upon treatment with a strong base such as n-butyllithium at a temperature of −78° to −30° for from about 30 minutes to about 24 hours, yields the desired vinyl lithium compound (step 10). Alternatively, the product of step 8 is treated with disiamylborane in an inert organic solvent followed by sequential treatment with trimethylamine oxide and a mixture of sodium hydroxide and iodine to provide the vinyl iodine of reaction step 11. This vinyl iodide, treated in the same manner as the vinyl stannane of reaction step 9 is converted to the vinyl lithium reagent.

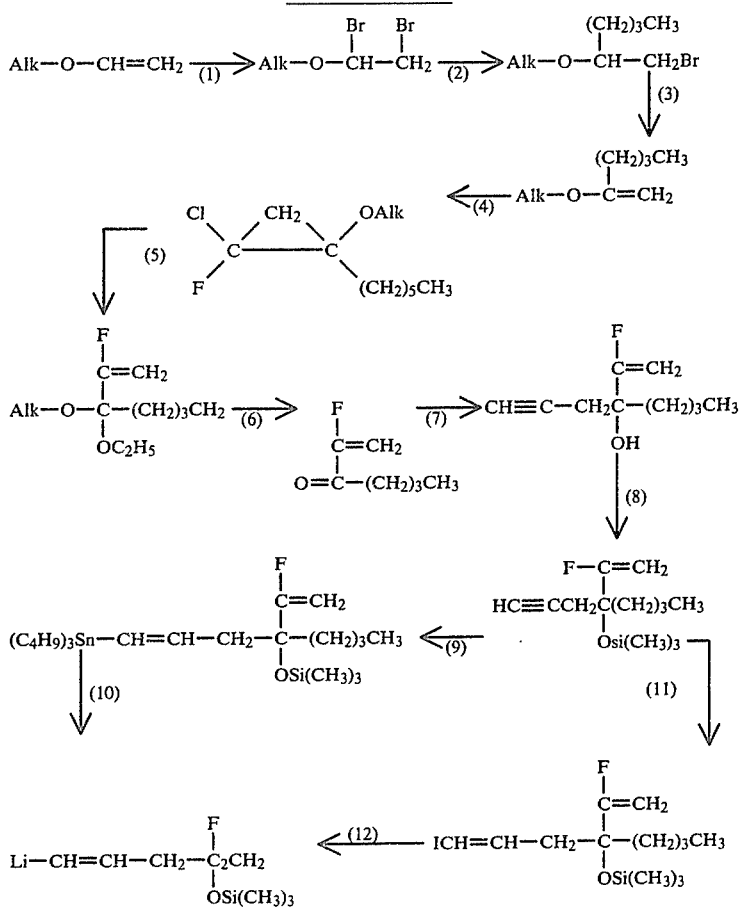

FLOWSHEET A

Flowsheet B

-continued
Flowsheet B

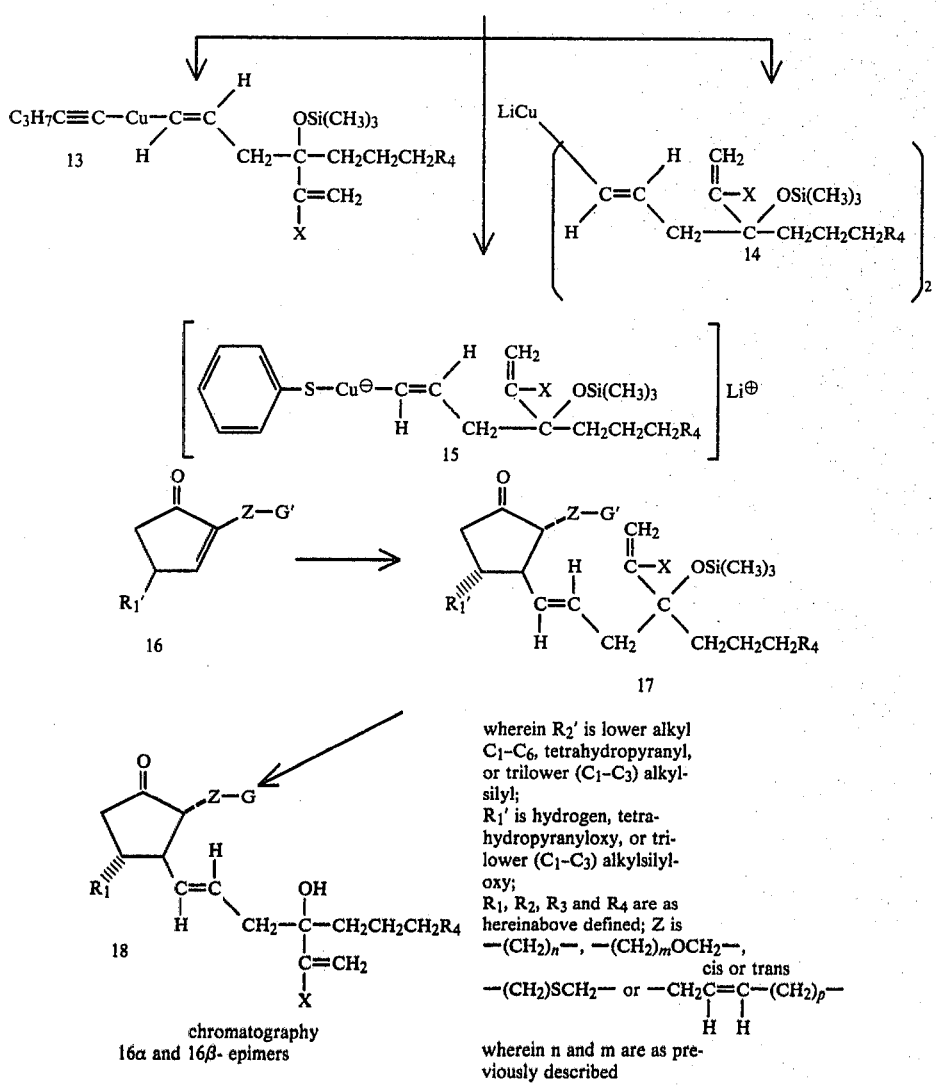

wherein $R_2'$ is lower alkyl $C_1$-$C_6$, tetrahydropyranyl, or trilower ($C_1$-$C_3$) alkylsilyl;

$R_1'$ is hydrogen, tetrahydropyranyloxy, or trilower ($C_1$-$C_3$) alkylsilyloxy;

$R_1$, $R_2$, $R_3$ and $R_4$ are as hereinabove defined; Z is
—$(CH_2)_n$—, —$(CH_2)_m OCH_2$—,
—$(CH_2)SCH_2$— or —$CH_2\underset{H}{C}=\underset{H}{C}$—$(CH_2)_p$— cis or trans wherein n and m are as previously described In accordance with Flowsheet B for the preparation of the asymmetrical lithio cuprate 13, wherein X and $R_4$ are as previously defined or the like, a solution of one molar equivalent of copper (I)-1-alkyne, preferably copper (I)-1-pentyne in anhydrous tributylphosphine or HMPTA, preferably one to five molar equivalents, in ether is added to one molar equivalent of the aforementioned vinyl lithium solution cooled to about $-78°$ C. After about one hour at this temperature, a molar equivalent of the requisite cyclopentenone 16 is added. After several hours at $-30°$ C. to $-70°$ C. the reaction mixture is quenched with aqueous ammonium chloride solution and the blocked product 17 is isolated in the usual manner.

It is also possible to effect conjugate 1,4-addition with the asymmetrical lithio cuprate 15 wherein X and $R_4$ are as previously defined derived from vinyl lithium and cuprous thiophenoxide. A solution of vinyl lithium 12 in ether at $-78°$ C. is reacted with an equimolar amount of a reagent prepared by admixture, in ether at a temperature of $0°$ C. to $-70°$ C., of equimolar amounts of cuprous thiophenoxide and copper (I) iodide tributylphosphonium complex. After about 30 minutes at this temperature, the lithio cuprate is treated with the requisite cyclopentenone 16 as described hereinabove for the conjugate addition with 1-alkynyl lithio cuprate 13.

For the preparation of the symmetrical lithio cuprate 14 wherein X and $R_4$ are as previously defined one molar equivalent of copper (I) iodide tributylphosphine complex, dissolved in anhydrous ether, is added at about $-78°$ C. to two molar equivalents of the aforementioned vinyl lithium 12 solution cooled to $-78°$ C. After about one hour at this temperature, the lithio cuprate 14 is treated with the requisite cyclopentenone 16 as described hereinabove for the conjugate addition with the 1-alkynyl lithio cuprate.

The procedures for conjugate addition involving organocopper reagents are well known in the art, see for example C. J. Sih, et al., J. Amer. Chem. Soc., 97, 865 (1975).

In the cases where $R'_1$=trimethylsilyloxy in cyclopentenone 16 the conjugate addition is performed at $-78°$ C. to $-40°$ C. The reaction is quenched by addition of an ether solution of acetic acid. Removal of blocking groups is then carried out as described in the reference above to provide the product 18 wherein $R_1$, G, X, Z and $R_4$ are as hereinabove.

The introduction of a racemic β-chain possessing the 16-hydroxy-16-halovinyl moieties provides a pair of prostaglandins epimeric at C-16. These two epimers may be separated into their upper (less polar) and lower (more polar) components by high-pressure liquid chromatography (HPLC) or by dry-column or preparative thin layer silica-gel chromatography.

If an optically active protected cyclopentenone such as 16 is utilized, then HPLC separation will provide the corresponding optically active nat. 9-oxo-11α,16α-dihydroxy-16-halovinyl and nat. 9-oxo-11α,16β-dihydroxy-16-halovinyl-PGA enantiomers.

From the available evidence it is apparent that the

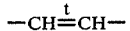

function introduced by the cuprate process occupies a position trans to the 11-oxy function. Similarly, in the product 18 the two side-chains attached to $C_8$ and $C_{12}$ are trans to each other. However, it is not absolutely possible to be certain of this configurational relationship in the product as it is obtained directly from the cuprate process. These products may have the side-chains in a trans- or cis-relationship or they may be a mixture containing both the trans- and cis-isomers. This is indicated in the nomenclature of the compounds involved by the designation 8ε. In order to ensure a trans-relationship in 18 these products can be submitted to conditions known in the literature to equilibrate the cis-8-iso-$PGE_1$ to a mixture containing about 90% of the trans product. These conditions involve treatment with potassium acetate in aqueous methanol for 96 hours at room temperature.

The triloweralkylsilyloxy substituted lithio cuprate reagents of type 13, 14 and 15 and the trialkylstannyl precursors 10 and 11 are novel and useful compounds which are also embraced by this invention. They may be defined by generic formulae 19 and 20.

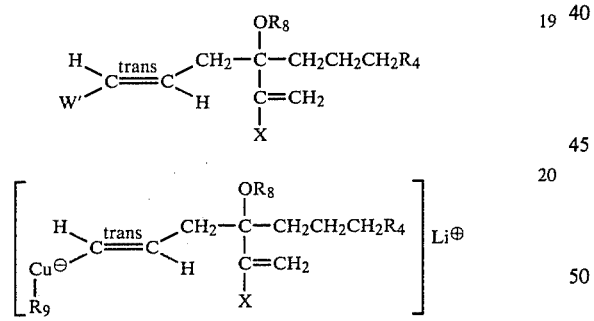

wherein W' is tri n-butylstannyl or lithium, X and $R_4$ are as hereinabove defined, $R_8$ is triloweralkylsilyl, $R_9$ is thiopheneoxide, substituted thiopheneoxide, an alkyne or the identical vinyl moiety.

The cyclopentenones required for the preparation of the $E_1$, $E_2$, 3-oxa, and 11-deoxy-3-thia series have been described in the literature. The cyclopentenone for the preparation of 3-thia-11-hydroxy prostaglandins is described in Flowsheet C.

The preparation of the cyclopentenones useful as precursors to the $PGE_1$ derivatives wherein the —COOH group is replaced by —CH₂OH (and protected forms) is described by Kluender et al., *Tetrahedron Letters*, No. 24, 2063–66 (1977). The preparation of the $E_2$ cyclopentenone wherein the —COOH is replaced by a —CH₂OH (or protected form) is described in U.S. Patent Applications Ser. No. 858,487 filed Dec. 8, 1977 and incorporated herein by reference.

The preparation of cyclopentenones wherein the —COOH group is replaced by a —CH₂OH or —CH₂OR₃ or —CH₂SR₁₅ are described in Ser. No. 046,511 filed on even date herewith and incorporated herein by reference.

In accordance with Flowsheet C which is hereinbelow described, treatment of 2-furyl lithium 21 with a ω-chloroaldehyde 22 provides the chloroalcohol 23. Treatment of the chloroalcohol 23 with ethylmercaptoacetate furnishes they hydroxyester 24 which upon hydrolysis with sodium formate/formic acid provides the 3-hydroxy-cyclopentenone 25. Treatment of the cyclopentenone 25 with sulfuric acid provides the required 4-hydroxy-cyclopentenone 26 which after treatment with chlorotrimethylsilane provides the bissilylated cyclopentenone 27.

FLOWSHEET C

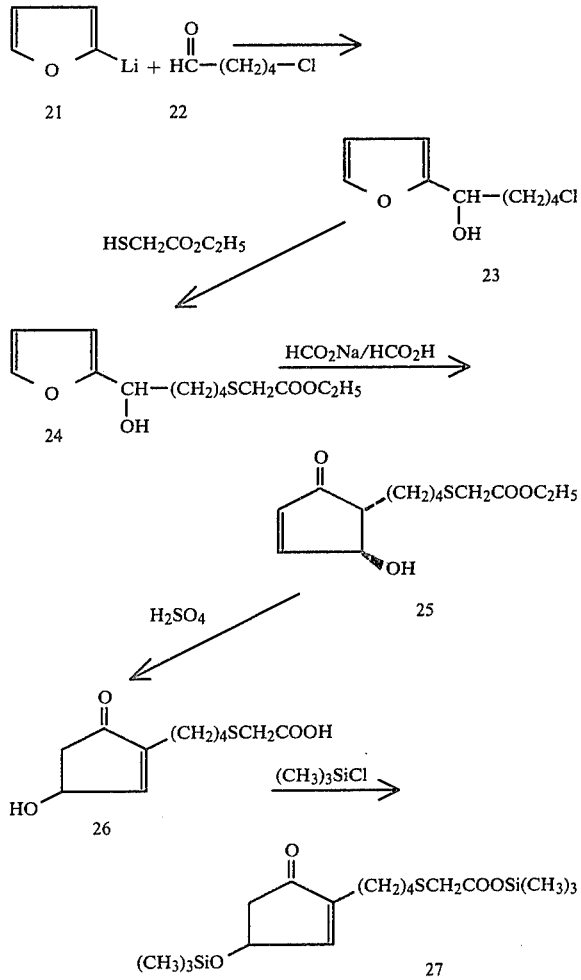

In accordance with Flowsheet D, when the 11-hydroxy or 11-oxy derivatives are treated with dilute acid, it is possible to effect elimination and the formation of the corresponding $\Delta^{10}$ derivatives of the prostaglandin A-type. A preferred procedure involves treatment in tetrahydrofuran:water (2:1) solvent 0.5 N in HCl for about 30 hours at ambient temperature. Under these conditions a tetrahydropyranyl or trialkylsilyl ester or ether will undergo hydrolysis.

FLOWSHEET D 17 or 18 →

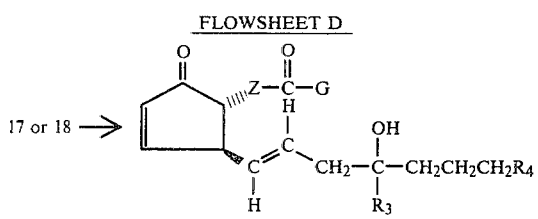

The prostaglandin carboxylic acids of this invention can be readily converted to the various alkyl esters of this invention by treatment in the usual manner with the appropriate diazoalkane. The preparation of diazoalkanes by various procedures are well described in the art. See for example C. D. Gutsche, *Organic Reactions*, VIII, 389 (1954). Certain of the esters of this invention can also be obtained directly by use of the appropriate cyclopentenone ester. The various esters can also be prepared by any of several procedures well-known in the art via an acid chloride (prior blocking of free alcohol groups with appropriate blocking groups such as trialkylsilyl, tetrahydropyranyl and the like) or mixed anhydrides and treatment of these intermediates with the appropriate alcohol. Mixed anhydrides can be obtained by treatment of the prostaglandin acid in a solvent such as dioxane at a temperature in the range of 0° C. to 15° C. with a molar equivalent of a tri-alkylamine, preferably triethylamine, tributylamine and the like, and then a molar equivalent of isobutyl chlorocarbonate or the like. The resulting mixed anhydrides are then treated with the appropriate alcohol to give the derivatized product. [For a pertinent literature analogy see *Prostaglandins*, 4, 768 (1973).]

An alternative procedure involves treatment of the prostaglandin acid with a molar equivalent of the trialkyl amine in an excess of the appropriate alcohol in an anhydrous solvent such as methylene chloride, a molar equivalent of p-toluenesulfonyl chloride is then added (if necessary, a second molar equivalent can be added) and after stirring at ambient temperatures for about 15 minutes to one hour the product is worked-up in the usual manner. (For a pertinent literature analogy, see U.S. Pat. No. 3,821,279.) A third procedure involves the use of dicyclohexylcarbodiimide in the usual manner; for a pertinent literature analogy see German Offen. No. 2,365,205; *Chem. Abst.*, 81, 120098g (1974).

The esterified alcohol derivatives of this invention are also prepared in the usual manner by procedures well known in the art from the appropriate alkanoic acid anhydride or acid chloride.

When the compounds of this invention are prepared from racemic starting compounds, two racemates are obtained. In appropriate instances these racemates may be separated from each other by careful application of the usual chromatographic procedures. In the more difficult instances it may be necessary to apply high pressure liquid chromatography including recycling techniques. [See G. Fallick, American Laboratory, 19-27 (August 1973) as well as references cited therein. Additional information, concerning high speed liquid chromatography and the instruments necessary for its application, is available from Waters Associate Inc., Maple Street, Milford, Mass.].

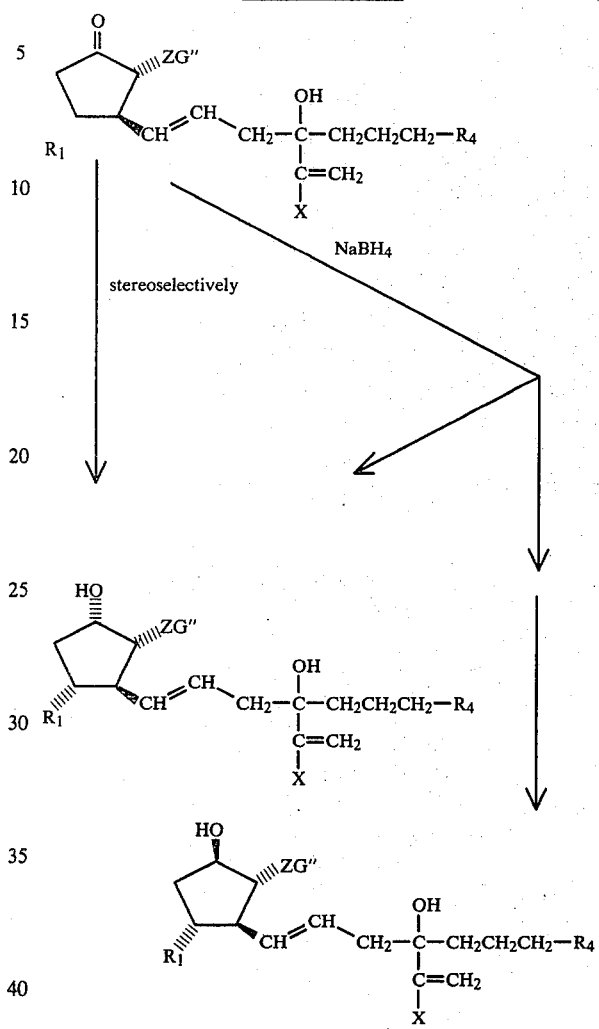

FLOWSHEET E

In accordance with Flowsheet E treatment of a prostaglandin of the E series (9-oxo wherein G" is selected from the group consisting of —COOR$_2$, and —CH$_2$OH, wherein R$_2$ is as previously defined with a carbonyl reducing reagent such as sodium borohydride provides a mixture of the corresponding PGFα(9α-hydroxy) and PGFα (9β-hydroxy) analogs. These two epimeric alcohols are readily separated by silica gel chromatography.

If one utilized the individual 16α-hydroxy or 16β-hydroxy E starting material, the isolated products are the 9α, 16α-dihydroxy and 9α, 16β-dihydroxy derivatives, respectively.

Use of a stereoselective reagent such as lithium-perhydro-9b-boraphenalylhydride [H. C. Brown and W. C. Dickason, J.A.C.S., 92, 709 (1970)] or lithium tri-sec-butylborohydride [H. C. Brown and S. Krishnamurthy, Ibid, 94, 7159 (1972)] provides the PGFα product as the selective species.

Likewise, utilization of either the individual 16α-or 16β-hydroxy E compounds affords the corresponding 9α,16α-dihydroxy and 9α,16β-dihydroxy prostaglandins of this invention.

FLOWSHEET F

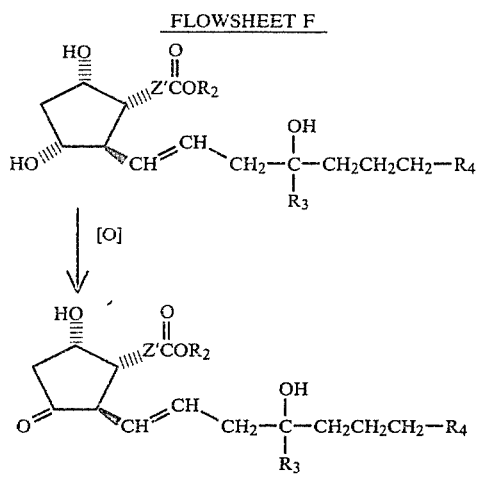

In accordance with Flowsheet F when 11α-hydroxy-PGF2α congeners wherein Z' is —(CH$_2$)n—, —CH$_2$C≡C(CH$_2$)$_p$— and —(CH$_2$)mOCH$_2$—, wherein m, n and p are as previously defined are treated with an oxidizing reagent such as Jones Reagent, or pyridinium chlorochromate provides a selective oxidation to give the corresponding PGD derivative (9α-hydroxy-11-keto) after chromatographic purification.

If one utilized the individual 16α-hydroxy or 16β-hydroxy PGFα derivatives, then the corresponding 9α,16β-dihydroxy-11-oxo and 9α,16α-dihydroxy-11-oxo-prostaglandins are isolated, respectively.

In the following formulae Z is as hereinabove defined.

The 4-hydroxycyclopentenone racemates may be resolved into their components enantiomers by derivatizing the ketone function with a reagent having an optically active center. The resulting diastereoisomeric mixture can then be separated by fractional crystallization, or by chromatography, or by high speed liquid chromatography involving, if necessary, recycling techniques. Among the useful optically active ketone derivatizing reagents are 1-α-aminoxy-α-methylpentanoic acid hydrochloride, (R)-2-aminoxy-3,3-dimethylbutyric acid hydrochloride, and 4-α-methylbenzyl semicarbazide. After separation of the diastereomeric derivatives, reconstitution of the keto function provides the individual 4-hydroxycyclopentenone enantiomers. A useful procedure for the resolution of a 4-hydroxycyclopentenone racemate via the oxime is described in the art [R. Pappo, P. Collins and C. Jung, *Tetrahedron Letters*, 943 (1973)]. The resolution of the hydroxycyclopentenone is described by Bruhn et al, *Tetrahedron Letters*, 235 (1976).

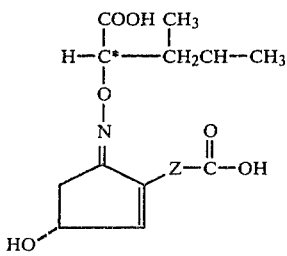

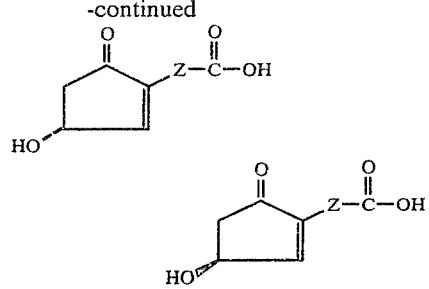

In the specification and claims herein the following definitions are intended to apply. The term "C$_1$ to C$_6$ alkyl" refers to a monovalent radical derived from an aliphatic hydrocarbon by removal of a hydrogen atom and includes both branched as well as straight chain radical such including methyl, ethyl, propyl, i-propyl, t-butyl and the like. The term "C$_1$ to C$_6$ alkoxy" refers to the above alkyl radicals attached to an oxygen radical with the other valence bond an oxygen being attached to the remainder of the molecule such including methoxy, ethoxy, i-propoxy, etc.

The following preparations and examples are set forth for purposes of illustration only and are not to be construed as limitations for the present invention except as set forth in the appended claims. All parts and percentages are by weight unless otherwise indicated.

PREPARATION 1

1,2-Dibromo-2-ethoxyethane

To 143 ml. of ethylvinyl ether at −25° C. is added, dropwise with stirring, during 2 hours, 82 ml. of bromine, at such a rate as to maintain the temperature at −10° C. The excess bromine is titrated with ethylvinyl ether. The product is distilled directly from the reaction vessel. After a 30 g. forerun, the main fraction of 266 g. of colorless liquid is collected, b.p. 55°-57° C., 10 mm.

PREPARATION 2

1-Bromo-2-ethoxyhexane

To a stirred solution of 1.68 moles of n-butylmagnesium bromide, as a 1.7M solution in ether, is added dropwise a solution of 300 g. of 1,2-dibromo-2-ethoxyethane in 750 ml. of ether during a period of 2 hours at −15° C. The resulting mixture is stirred for one hour while warming to 20° C., then cooled to 0° C., and treated while stirring with 500 ml. of water, followed by 100 ml. of 4N hydrochloric acid. The organic layer is washed with brine, dried over magnesium sulfate and concentrated. The residue is distilled to provide a colorless liquid, b.p. 83°-84° C., 18 mm.

PREPARATION 3

2-Ethoxy-1-hexene

A 17.3 g. portion of 50% sodium hydride in mineral oil is washed free of the mineral oil under a nitrogen atmosphere with three 150 ml. portions of petroleum ether. This sodium hydride is then suspended in 300 ml. of dry dimethylformamide. A solution of 62.7 g. of 1-bromo-2-ethoxyhexane in 150 ml. of dimethylformamide is added followed by one ml. of isopropanol. The mixture is stirred and heated cautiously using an oil bath, starting at 25° C. Upon reaching an internal temperature of 82° C., a vigorous exothermic reaction begins. This reaction is maintained by a water bath at 85°

C. to 90° C. When the reaction slows, the mixture is heated externally at 85° C. to 90° C. for 45 minutes. The reaction mixture is cooled to 0° C., treated cautiously with a total of 1.5 liters of water and then extracted with three 400 ml. portions of ether. The organic extracts are combined, washed with three 250 ml. portions of water, then two 250 ml. portions of brine and dried over potassium carbonate. To the organic solution is added 6 drops of pyridine and 100 mg. of hydroquinone. This mixture is filtered and concentrated in vacuo, giving an orange liquid. Distillation of this crude product gives 21 g. of the desired product, b.p. 83°–85° C., 140 mm.

PREPARATION 4

2-Butyl-1-chloro-2-ethoxy-1-fluoro cyclopropane

To a solution of 61.0 g. of 2-ethoxy-1-hexene, 135 ml. of 13.5M potassium hydroxide and 2.7 g. of "18-crown-6" ether at −15° C. is added dropwise over 30 minutes at 0° a 90 ml., portion of dichlorofluoromethane. After the addition, the mixture is placed in an ice bath. An exotherm raises the temperature to 20° C., whereupon the mixture is placed in a dry-ice/carbon tetrachloride bath to maintain the temperature at −5° C. to 0° C. After three hours at this temperature, the reaction mixture is diluted with water and extracted with ether. The ether extracts are combined, washed with water, then brine, dried over potassium cabonate and concentrated in vacuo to an oil. This oil is distilled through a 6 inch Vigreux column to provide 82 g. of the desired compound as a colorless liquid, b.p. 70°–71° C., 16 mm.

PREPARATION 5

3,3-Diethoxy-2-fluoro-1-hexene

A stirred solution of 58.4 g. of 2-butyl-1-chloro-2-ethoxy-1-fluorocyclopropane and 166 g. of anhydrous potassium carbonate in 400 ml. of absolute ethanol is heated at reflux for 18 hours. The solution is cooled and the bulk of the ethanol is removed in vacuo. The residue is partitioned with 500 ml. of water and 750 ml. of ether. The ether phase is washed with three 100 ml. portions of brine, dried over potassium carbonate and concentrated in vacuo to provide 54 g. of a pale yellow oil. A 4.45 g. portion of this oil is distilled through a 6 inch Vigreux column having 2.5 g. of the desired product as a colorless liquid, b.p. 80°–81° C., 24 mm.

PREPARATION 6

2-Fluorohex-1-en-2-one

A solution comprising 49 g. of 3,3-diethoxy-2-fluoro-1-hexene, 60 ml. of 4N hydrochloric acid, 720 ml. of tetrahydrofuran and 0.25 g. of hydroquinone as allowed to stand at room temperature for 17 hours. The solution is then concentrated in vacuo to 150 ml. and diluted with ether and brine. The ether layer is washed with brine, dried over magnesium sulfate and concentrated in vacuo giving 28 g. of a light yellow liquid. This liquid is distilled giving 19 g. of the desired compound. (This ketone should be used immediately in the procedure of Preparation 7 and hydroquinone should be added to the distillate to prevent polymerization.

PREPARATION 7

4-Hydroxy-4-(1'-fluorovinyl)-1-octyne

The Grignard reaction is accomplished according to the procedure disclosed in U.S. Pat. No. 4,061,670 which is incorporated herein by reference.

To a stirred suspension of 62 mg. of mercuric chloride and 4.97 g. of magnesium metal shavings in 30 ml. of ether, at room temperature, is added a solution of 29.1 g. of 80% propargyl bromide in toluene in 90 ml. of ether. After the grignard formation is complete, the grignard solution is cooled to −20° C. and a solution of 18.9 g. of 2-fluorohex-1-en-2-one in 65 ml. of ether is added. The reaction mixture is stirred at room temperature for 1.5 hours, recooled to 0° C., quenched cautiously with 5 ml. of saturated ammonium chloride and diluted with 50 ml. of ether. The ether phase is washed with brine, filtered through diatomaceous earth, dried over a mixture of potassium carbonate and magnesium sulfate and concentrated in vacuo, giving 30 g. of an oil. A small amount of potassium carbonate is added to this oil which is then distilled through a 6 inch Vigreux column giving 14 g. of the desired product as a colorless liquid, b.p. 70°–73° C., 14 mm.

PREPARATION 8

4-(1'-Fluorovinyl)-4-trimethylsilyloxy-1-octyne

To a stirred 0° C. solution of 13.7 g. of 4-(1-fluorovinyl)-4-hydroxy-1-octyne and 16.1 g. of imidazole in 60 ml. of anhydrous dimethylformamide is added, via a syringe over a 3 minute period, 11.6 ml. of chlorotrimethylsilane. The resulting solution is stirred at room temperature for 18 hours, cooled to 0° C., diluted with 350 ml of petroleum ether and shaken with 150 ml. of water. The organic phase is separated, washed with six 50 ml. portions of water, then 50 ml. of brine, dried over magnesium sulfate and concentrated in vacuo giving 18.9 g. of the desired product as a colorless liquid.

PREPARATION 9

E-4-(1'-Fluorovinyl)-1-tributylstannyl-4-trimethylsilyloxy-1-octene

A mixture of 21.4 ml. of tributylstannane, 18.3 g. of 4-(1'-fluorovinyl)-4-trimethylsilyloxy-1-octyne and azobisisobutyronitrile is heated under an inert atmosphere on an oil bath. Upon reaching 85° C. a rapid exotherm occurs which is moderated to maintain 140° C. using a water bath. After the exotherm the mixture is heated at 135° C. for one hour, then cooled to room temperature. The resulting oil is distilled via a Kugelrohr to give the desired product as 33.68 g. of a light yellow liquid (air bath 160° C., 0.15 mm.).

EXAMPLE 1A

15-Deoxy-16-(1'-fluorovinyl)-16-hydroxyprostaglandin-$E_1$

To a stirred solution of 5.39 g. of (E)-1-(tri-n-butylstannyl)-4-(1'-fluorovinyl)-4-(trimethylsilyloxy)-1-octene in 5 ml. of dry tetrahydrofuran, cooled to −78° C. in an argon atmosphere, is added dropwise, during 10 minutes, 5.06 ml. of 1.92M n-butyllithium in hexane. The resulting solution is stirred at −78° C. for 10 minutes, then at −35° C. for 2½ hours. The solution is recooled to −78° C. and a solution of 1.32 g. of 1-pentynylcopper and 5.04 ml. of tri-n-butylphosphine in 15 ml. of ether is added during 10 minutes. The resulting solution, containing lithiopentynyl [(E)-4-(1'-fluorovinyl)-4-(trimethylsilyloxy)-1-octenyl]cuprate is stirred at −78° C. for one hour at which time 3 g. of 4-(trimethylsilyloxy)-2-(6'-carbotrimethylsilyloxyhexenyl)cyclopent-2-en-1-one in 3 ml. of ether is added during 10 minutes. The solution is stirred at −78° C. for 10 minutes, then at −35° C. for 2 hours, recooled to −55° C. and quenched by pouring into 100 ml. of cold saturated ammonium chloride solution and 100 ml. of ether.

The ether layer is separated and saved. The aqueous layer is extracted twice with ether. The combined organic extracts are washed with dilute hydrochloric acid, then brine, dried with anhydrous sodium sulfate and taken to dryness, leaving an oil. This oil is treated with 60 ml. of acetic acid, 30 ml. of tetrahydrofuran and 15 ml. of water, stirred at room temperature for one hour, then diluted with toluene and taken to dryness.

The residual oil is dissolved in 45 ml. of methanol and the resulting solution is extracted twice with 45 ml. portions of heptane. The extracts are discarded. The methanol solution is taken to dryness leaving 5.64 g. of oil. This oil is applied to a 2 inch flat dry column containing 750 g. of silica gel and developed with ethyl acetate:hexane:acetic acid (60:40:1). The bottom 20 inches of the column is removed and discarded. The remainder of the column is divided into one inch segments. Segments 20–25 are combined to provide 392 mg. of the desired product as an oil.

EXAMPLE 1B

15-Deoxy-16-(1'-fluorovinyl)-16-hydroxyprostaglandin-E$_2$

To a stirred solution of 8.7 g. of (E)-1-tri-n-butylstannyl)-4-(1'-fluorovinyl)-4-trimethylsilyloxy-1-octene in 10 ml. of dry tetrahydrofuran, cooled to −78° C. under an argon atmosphere, is added dropwise over a period of 15 minutes, 7.7 ml. of 1.9M n-butyllithium. The resulting solution is stirred at −78° C. for 20 minutes, then at −45° C. to −35° C. for 2½ hours. The solution is recooled to −78° C., and a chilled solution of 2.9 g. of pentynylcopper and 9.0 g. of tri-n-butylphosphine in 20 ml. of dry ether is added dropwise over a period of 5 minutes. This turbid solution is stirred at −78° C. for 1½ hours. A solution of 4.0 g. of 4-(trimethylsiloxy)-2-(6'-carbotrimethylsiloxy-2'-(z)-hexenyl)cyclopent-2-en-1-one in 10 ml. of dry ether is chilled in a dry-ice/acetone bath and added dropwise during a period of 5 minutes. This solution is stirred at −78° C. for 20 minutes, then at −45° C. to −35° C. for one hour, then slowly allowed to warm to −23° C. over a period of 45 minutes. The solution is recooled to −78° C. and the reaction is quenched by pouring the solution into an ice cold mixture of 200 ml. of saturated ammonium chloride solution and 200 ml. of ether. The mixture is stirred rapidly for 20 minutes, then stored in a refrigerator overnight.

The layers are separated and the aqueous layer is extracted with two 250 ml. portions of ethyl acetate. The combined organic layers are washed with 250 ml. of cold dilute hydrochloric acid and then twice with 250 ml. of a solution of 50% saturated ammonium chloride and 50% saturated sodium bicarbonate, dried over magnesium sulfate and concentrated in vacuo. The resulting oil is treated with 80 ml. of glacial acetic acid, 40 ml. of tetrahydrofuran and 20 ml. of water and stirred in an argon atmosphere at room temperature for one hour. A 75 ml. portion of toluene is added and the mixture is concentrated in vacuo, using a water bath at 34°–35° C. to one-half its volume. Another 50 ml. of toluene is added and the above concentration is repeated. Toluene (25 ml.) is added twice more, the mixture, however, being concentrated to an oil after each addition. The remaining oil is partitioned betwee 50 ml. of heptane and 50 ml. of methanol. The methanol layer is saved and the heptane layer is extracted with an additional 10 ml. of methanol. The combined methanol layers are concentrated in vacuo to an oil. This oil is dissolved in 10 ml. of a mixture of ethyl acetate:hexane:acetic acid (80:20:0.1) and put on a Waters Co. preparative high pressure liquid chromatograph (model 500) via a syringe. The instrument is loaded with a pre-packed silica gel column (Waters Co.). The above described solvent mixture is pumped through the column at a rate of 250 ml. per minute, collecting 500 ml. fractions. The product starts to come off after 800 ml. has been eluted and after an additional 2 liters, the elution of the product is essentially complete. This includes some less and more polar impurities. Some toluene is added to each fraction. The fractions are then concentrated giving a total of 0.5 g. of crude oil. This oil is recolumned on 750 g. of dry column silica gel using a 2 inch flexible dry column tube and a solvent mixture of 70 parts ethyl acetate, 30 parts heptane and one part acetic acid. The oil is dissolved in 5 ml. of solvent and transferred to the column. The solvent is allowed to elute to the bottom of the column. The bottom 6 inches of the 62 inch column is cut off and discarded. The remainder of the column is cut into one inch segments. The product, (290 mg.) a mixture of two epimers, is collected in fractions 21–28. It is shown by C-13 n.m.r. spectroscopy to be a 40:60 mixture of upper to lower epimers.

The following examples illustrate the treatment of various vinyl tris compounds with various cyclopentones to form the listed prostaglandin compounds. These reactions are generally accomplished by following the procedure of Example IA and IB. In addition, the reduction of the various PGE analogs of the present invention to their corresponding PGF compounds is also set forth in their examples. The procedure of of much reduction is well known to those skilled in the art and has been treated extensively in, for example U.S. patent applications Ser. No. 961,032 filed Oct. 15, 1978 and Ser. No. 3,953 filed Jan. 16, 1979, incorporated hereby by reference.

| EXAMPLE | VINYL TIN | CYCLOPENTENONE | PRODUCT PROSTAGLANDIN OF THE PGE2 SERIES |
|---|---|---|---|
| 2 | 1-trans-tri-n-butylstannyl-4-(1-fluorovinyl)-4-trimethylsiloxy-1-octene | 2-(5-carbotrimethylsiloxypent-2-cis-enyl)-4-trimethylsiloxycyclopent-2-en-1-one | dl-11a,16-dihydroxy-9-oxo-16-(1-fluorovinyl)-2-nor-5-cis-13-trans prostadienoic acid |
| 3 | 1-trans-tri-n-butylstannyl-4-(1-fluorovinyl)-4-trimethylsiloxy-1-nonene | 2-(5-carbotrimethylsiloxypent-2-cis-enyl)-4-trimethylsiloxycyclopent-2-en-1-one | 20-methyl-2-nor-5-cis-13-trans prostadienoic acid |
| 4 | 1-trans-tri-n-butylstannyl-4-(1-fluorovinyl)-4-trimethylsiloxy-1-decene | 2-(5-carbotrimethylsiloxypent-2-cis-enyl)-4-trimethylsiloxycyclopent-2-en-1-one | dl-11a,16-dihydroxy-9-oxo-16-(1-fluorovinyl)-20-ethyl-2-nor-5-cis-13-trans prostadienoic acid |
| 5 | 1-trans-tri-n-butylstannyl-4-(1-fluorovinyl)-4-trimethylsiloxy-1-octene | 2-(6-carbotrimethylsiloxyhex-2-cis-enyl)-4-trimethylsiloxycyclopent-2-en-1-one | dl-11a,16-dihydroxy-9-oxo-16-(1-fluorovinyl)-5-cis-13-trans prostadienoic acid |
| 6 | 1-trans-tri-n-butylstannyl-4-(1-fluorovinyl)-4-trimethylsiloxy-1-heptene | 2-(6-carbotrimethylsiloxyhex-2-cis-enyl)-4-trimethylsiloxycyclopent-2-en-1-one | 20-nor-5-cis-13-trans prostadienoic acid |
| 7 | 1-trans-tri-n-butylstannyl-4-(1-fluorovinyl)-4-trimethylsiloxy-1-octene | 2-(6-carbotrimethylsiloxyhex-2-cis-enyl)-4-trimethylsiloxycyclopent-2-en-1-one | dl-11a,16-dihydroxy-9-oxo-16-(1-fluorovinyl)-5-cis-13-trans prostadienoic acid |
| 8 | 1-trans-tri-n-butylstannyl-4-(1-fluorovinyl)-4-trimethylsiloxy-1-nonene | 2-(6-carbotrimethylsiloxyhex-2-cis-enyl)-4-trimethylsiloxycyclopent-2-en-1-one | 20-methyl-5-cis-13-trans prostadienoic acid |
| 9 | 1-trans-tri-n-butylstannyl-4-(1-fluorovinyl)-4-trimethylsiloxy-1-decene | 2-(6-carbotrimethylsiloxyhex-2-cis-enyl)-4-trimethylsiloxycyclopent-2-en-1-one | 20-ethyl-5-cis-13-trans prostadienoic acid |
| 10 | 1-trans-tri-n-butylstannyl-4-(1-fluorovinyl)-4-trimethylsiloxy-1-heptene | 2-(7-carbotrimethylsiloxyhept-2-cis-enyl)-4-trimethylsiloxycyclopent-2-en-1-one | dl-11a,16-dihydroxy-9-oxo-16-(1-fluorovinyl)-20-nor-2-homo-5-cis-13-trans prostadienoic acid |
| 11 | 1-trans-tri-n-butylstannyl-4-(1-fluorovinyl)-4-trimethylsiloxy-1-octene | 2-(7-carbotrimethylsiloxyhept-2-cis-enyl)-4-trimethylsiloxycyclopent-2-en-1-one | dl-11a,16-dihydroxy-9-oxo-16-(1-fluorovinyl)-2-homo-5-cis-13-trans prostadienoic acid |
| 12 | 1-trans-tri-n-butylstannyl-4-(1-fluorovinyl)-4-trimethylsiloxy-1-nonene | 2-(7-carbotrimethylsiloxyhept-2-cis-enyl)-4-trimethylsiloxycyclopent-2-en-1-one | dl-11a,16-dihydroxy-9-oxo-16-(1-fluorovinyl)-20-methyl-2-homo-5-cis-13-trans prostadienoic acid |
| 13 | 1-trans-tri-n-butylstannyl-4-(1-fluorovinyl)-4-trimethylsiloxy-1-decene | 2-(7-carbotrimethylsiloxyhept-2-cis-enyl)-4-trimethylsiloxycyclopent-2-en-1-one | 20-ethyl-2-homo-5-cis-13-trans prostadienoic acid |
| 14 | 1-trans-tri-n-butylstannyl-4-(1-fluorovinyl)-4-trimethylsiloxy-1-heptene | 4R-trimethylsiloxycyclopent-2-en-1-one | nat-11a,16-dihydroxy-9-oxo-16-(1-fluorovinyl)-20-nor-5-cis-13-trans prostadienoic acid |
| 15 | 1-trans-tri-n-butylstannyl-4-(1-fluorovinyl)-4-trimethylsiloxy-1-octene | 2-(6-carbotrimethylsiloxyhex-2-cis-enyl)-4R-trimethylsiloxycyclopent-2-en-1-one | nat-11a,16-dihydroxy-9-oxo-16-(1-fluorovinyl)-5-cis-13-trans prostadienoic acid |
| 16 | 1-trans-tri-n-butylstannyl-4-(1-fluorovinyl)-4-trimethylsiloxy-1-nonene | 2-(6-carbotrimethylsiloxyhex-2-cis-enyl)-4R-trimethylsiloxycyclopent-2-en-1-one | nat-11a,16-dihydroxy-9-oxo-16-(1-fluorovinyl)-20-methyl-5-cis-13-trans prostadienoic acid |

| EXAMPLE | VINYL TIN | CYCLOPENTENONE | PRODUCT PROSTAGLANDIN OF THE 11-DEOXY PGE2 SERIES |
|---|---|---|---|
| 17 | 1-trans-tri-n-butylstannyl-4-(1-fluorovinyl)-4-trimethylsiloxy-1-heptene | 2-(5-carboethoxypent-2-cis-enyl)cyclopent-2-en-1-one | dl-16-hydroxy-9-oxo-16-(1-fluorovinyl)-20-nor-2-nor-5-cis-13-trans prostadienoic acid |
| 18 | 1-trans-tri-n-butylstannyl-4-(1-fluorovinyl)-4-trimethylsiloxy-1-octene | 2-(5-carboethoxypent-2-cis-enyl)cyclopent-2-en-1-one | dl-16-hydroxy-9-oxo-16-(1-fluorovinyl)-2-nor-5-cis-13-trans prostadienoic acid |
| 19 | 1-trans-tri-n-butylstannyl-4-(1-fluorovinyl)-4-trimethylsiloxy-1-nonene | 2-(5-carboethoxypent-2-cis-enyl)cyclopent-2-en-1-one | dl-16-hydroxy-9-oxo-16-(1-fluorovinyl)-20-methyl-2-nor-5-cis-13-trans prostadienoic acid |
| 20 | 1-trans-tri-n-butylstannyl-4-(1-fluorovinyl)-4-trimethylsiloxy-1-decene | 2-(5-carboethoxypent-2-cis-enyl)cyclopent-2-en-1-one | 20-ethyl-2-nor-5-cis-13-trans prostadienoic acid |
| 21 | 1-trans-tri-n-butylstannyl-4-(1-fluorovinyl)-4-trimethylsiloxy-1-heptene | 2-(6-carboethoxyhex-2-cis-enyl)cyclopent-2-en-1-one | dl-16-hydroxy-9-oxo-16-(1-fluorovinyl)-20-nor-5-cis-13-trans prostadienoic acid |
| 22 | 1-trans-tri-n-butylstannyl-4-(1-fluorovinyl)-4-trimethylsiloxy-1-octene | 2-(6-carboethoxyhex-2-cis-enyl)cyclopent-2-en-1-one | dl-16-hydroxy-9-oxo-16-(1-fluorovinyl)-5-cis-13-trans prostadienoic acid |
| 23 | 1-trans-tri-n-butylstannyl-4-(1-fluorovinyl)-4-trimethylsiloxy-1-octene | 2-(6-carboethoxyhex-2-cis-enyl)cyclopent-2-en-1-one | dl-16-hydroxy-9-oxo-16-(1-fluorovinyl)-5-cis-13-trans prostadienoic acid |
| 24 | 1-trans-tri-n-butylstannyl-4-(1-fluorovinyl)-4-trimethylsiloxy-1-nonene | 2-(6-carboethoxyhex-2-cis-enyl)cyclopent-2-en-1-one | dl-16-hydroxy-9-oxo-16-(1-fluorovinyl)-20-methyl-5-cis-13-trans prostadienoic acid |
| 25 | 1-trans-tri-n-butylstannyl-4-(1-fluorovinyl)-4-trimethylsiloxy-1-decene | 2-(6-carboethoxyhex-2-cis-enyl)cyclopent-2-en-1-one | 20-ethyl-5-cis-13-trans prostadienoic acid |
| 26 | 1-trans-tri-n-butylstannyl-4-(1-fluorovinyl)-4-trimethylsiloxy-1-octene | 2-(7-carboethoxyhept-2-cis-enyl)cyclopent-2-en-1-one | dl-16-hydroxy-9-oxo-16-(1-fluorovinyl)-20-nor-2-homo-5-cis-13-trans prostadienoic acid |
| | 1-trans-tri-n-butylstannyl-4-(1-fluorovinyl)-4-trimethylsiloxy-1-octene | 2-(7-carboethoxyhept-2-cis-enyl)cyclopent-2-en-1-one | dl-16-hydroxy-9-oxo-16-(1-fluorovinyl)-2-homo-5-cis-13-trans prostadienoic acid |

-continued

| EXAMPLE | VINYL TIN | CYCLOPENTENONE | PRODUCT PROSTAGLANDIN OF THE PGE2 SERIES |
|---|---|---|---|
| 27 | 1-trans-tri-n-butylstannyl-4-(1-fluorovinyl)-4-trimethylsiloxy-1-nonene | 2-(7-carboethoxyhept-2-cis-enyl)cyclopent-2-en-1-one | dl-16-hydroxy-9-oxo-16-(1-fluorovinyl)-20-methyl-2-homo-5-cis-13-trans prostadienoic acid |
| 28 | 1-trans-tri-n-butylstannyl-4-(1-fluorovinyl)-4-trimethylsiloxy-1-decene | 2-(7-carboethoxyhept-2-cis-enyl)cyclopent-2-en-1-one | dl-16-hydroxy-9-oxo-16-(1-fluorovinyl)-20-ethyl-2-homo-5-cis-13-trans prostadienoic acid |

| EXAMPLE | VINYL TIN | CYCLOPENTENONE | PRODUCT PROSTAGLANDIN OF THE PGE2 SERIES |
|---|---|---|---|
| 29 | 1-trans-tri-n-butylstannyl-4-(1-fluorovinyl)-4-trimethylsiloxy-1-heptene | 2-(5-carbotrimethylsiloxypent-2-cis-enyl)-4-trimethylsiloxycyclopent-2-en-1-one | dl-11a,16-dihydroxy-9-oxo-16-(1-fluorovinyl)-20-nor-2-nor-5-cis-13-trans prostadienoic acid |
| 30 | 1-trans-tri-n-butylstannyl-4-(1-fluorovinyl)-4-trimethylsiloxy-1-heptene | 2-(5-carbotrimethylsiloxypent-2-cis-enyl)-4-trimethylsiloxycyclopent-2-en-1-one | dl-11a,16-dihydroxy-9-oxo-16-(1-fluorovinyl)-20-nor-2-nor-5-cis-13-trans prostadienoic acid |
| 31 | 1-trans-tri-n-butylstannyl-4-(1-fluorovinyl)-4-trimethylsiloxy-1-octene | 2-(5-carbotrimethylsiloxypent-2-cis-enyl)-4-trimethylsiloxycyclopent-2-en-1-one | dl-11a,16-dihydroxy-9-oxo-16-(1-fluorovinyl)-2-nor-5-cis-13-trans prostadienoic acid |
| 32 | 1-trans-tri-n-butylstannyl-4-(1-fluorovinyl)-4-trimethylsiloxy-1-nonene | 2-(5-carbotrimethylsiloxypent-2-cis-enyl)-4-trimethylsiloxycyclopent-2-en-1-one | dl-11a,16-dihydroxy-9-oxo-16-(1-fluorovinyl)-20-methyl-2-nor-5-cis-13-trans prostadienoic acid |
| 33 | 1-trans-tri-n-butylstannyl-4-(1-fluorovinyl)-4-trimethylsiloxy-1-decene | 2-(5-carbotrimethylsiloxypent-2-cis-enyl)-4-trimethylsiloxycyclopent-2-en-1-one | dl-11a,16-dihydroxy-9-oxo-16-(1-fluorovinyl)-20-ethyl-2-nor-5-cis-13-trans prostadienoic acid |
| 34 | 1-trans-tri-n-butylstannyl-4-(1-fluorovinyl)-4-trimethylsiloxy-1-heptene | 2-(6-carbotrimethylsiloxyhex-2-cis-enyl)-4-trimethylsiloxycyclopent-2-en-1-one | dl-11a,16-dihydroxy-9-oxo-16-(1-fluorovinyl)-20-nor-5-cis-13-trans prostadienoic acid |
| 35 | 1-trans-tri-n-butylstannyl-4-(1-fluorovinyl)-4-trimethylsiloxy-1-octene | 2-(6-carbotrimethylsiloxyhex-2-cis-enyl)-4-trimethylsiloxycyclopent-2-en-1-one | dl-11a,16-dihydroxy-9-oxo-16-(1-fluorovinyl)-5-cis-13-trans prostadienoic acid |
| 36 | 1-trans-tri-n-butylstannyl-4-(1-fluorovinyl)-4-trimethylsiloxy-1-nonene | 2-(6-carbotrimethylsiloxyhex-2-cis-enyl)-4-trimethylsiloxycyclopent-2-en-1-one | dl-11a,16-dihydroxy-9-oxo-16-(1-fluorovinyl)-20-methyl-5-cis-13-trans prostadienoic acid |
| 37 | 1-trans-tri-n-butylstannyl-4-(1-fluorovinyl)-4-trimethylsiloxy-1-decene | 2-(6-carbotrimethylsiloxyhex-2-cis-enyl)-4-trimethylsiloxycyclopent-2-en-1-one | dl-11a,16-dihydroxy-9-oxo-16-(1-fluorovinyl)-20-ethyl-5-cis-13-trans prostadienoic acid |
| 38 | 1-trans-tri-n-butylstannyl-4-(1-fluorovinyl)-4-trimethylsiloxy-1-decene | 2-(7-carbotrimethylsiloxyhept-2-cis-enyl)-4-trimethylsiloxycyclopent-2-en-1-one | dl-11a,16-dihydroxy-9-oxo-16-(1-fluorovinyl)-20-nor-2-homo-5-cis-13-trans prostadienoic acid |
| 39 | 1-trans-tri-n-butylstannyl-4-(1-fluorovinyl)-4-trimethylsiloxy-1-octene | 2-(7-carbotrimethylsiloxyhept-2-cis-enyl)-4-trimethylsiloxycyclopent-2-en-1-one | dl-11a,16-dihydroxy-9-oxo-16-(1-fluorovinyl)-2-homo-5-cis-13-trans prostadienoic acid |
| 40 | 1-trans-tri-n-butylstannyl-4-(1-fluorovinyl)-4-trimethylsiloxy-1-octene | 2-(7-carbotrimethylsiloxyhept-2-cis-enyl)-4-trimethylsiloxycyclopent-2-en-1-one | dl-11a,16-dihydroxy-9-oxo-16-(1-fluorovinyl)-20-methyl-2-homo-5-cis-13-trans prostadienoic acid |
| 41 | 1-trans-tri-n-butylstannyl-4-(1-fluorovinyl)-4-trimethylsiloxy-1-nonene | 2-(7-carbotrimethylsiloxyhept-2-cis-enyl)-4-trimethylsiloxycyclopent-2-en-1-one | dl-11a,16-dihydroxy-9-oxo-16-(1-fluorovinyl)-20-ethyl-2-homo-5-cis-13-trans prostadienoic acid |
| 42 | 1-trans-tri-n-butylstannyl-4-(1-fluorovinyl)-4-trimethylsiloxy-1-decene | 2-(6-carbotrimethylsiloxyhex-2-cis-enyl)-4R-trimethylsiloxycyclopent-2-en-1-one | nat-11a,16-dihydroxy-9-oxo-16-(1-fluorovinyl)-20-nor-5-cis-13-trans prostadienoic acid |
| 43 | 1-trans-tri-n-butylstannyl-4-(1-fluorovinyl)-4-trimethylsiloxy-1-heptene | 2-(6-carbotrimethylsiloxyhex-2-cis-enyl)-4R-trimethylsiloxycyclopent-2-en-1-one | nat-11a,16-dihydroxy-9-oxo-16-(1-fluorovinyl)-5-cis-13-trans prostadienoic acid |
| 44 | 1-trans-tri-n-butylstannyl-4-(1-fluorovinyl)-4-trimethylsiloxy-1-octene | 2-(6-carbotrimethylsiloxyhex-2-cis-enyl)-4R-trimethylsiloxycyclopent-2-en-1-one | nat-11a,16-dihydroxy-9-oxo-16-(1-fluorovinyl)-20-methyl-5-cis-13-trans prostadienoic acid |
| 45 | 1-trans-tri-n-butylstannyl-4-(1-fluorovinyl)-4-trimethylsiloxy-1-decene | 2-(6-carbotrimethylsiloxyhex-2-cis-enyl)-4R-trimethylsiloxycyclopent-2-en-1-one | nat-11a,16-dihydroxy-9-oxo-16-(1-fluorovinyl)-20-ethyl-5-cis-13-trans prostadienoic acid |

| EXAMPLE | VINYL TIN | CYCLOPENTENONE | PRODUCT PROSTAGLANDIN OF THE 11-DEOXY PGE2 SERIES |
|---|---|---|---|
| 46 | 1-trans-tri-n-butlystannyl-4-(1-fluorovinyl)-4-trimethylsiloxy-1-heptene | 2-(5-carboethoxypent-2-cis-enyl)cyclopent-2-en-1-one | dl-16-hydroxy-9-oxo-16-(1-fluorovinyl)-20-nor-2-nor-5-cis-13-trans prostadienoic acid |
| 47 | 1-trans-tri-n-butylstannyl-4-(1-fluorovinyl)-4-trimethylsiloxy-1-octene | 2-(5-carboethoxypent-2-cis-enyl)cyclopent-2-en-1-one | dl-16-hydroxy-9-oxo-16-(1-fluorovinyl)-2-nor-5-cis-13-trans prostadienoic acid |
| 48 | 1-trans-tri-n-butylstannyl-4-(1-fluorovinyl)-4-trimethylsiloxy-1-nonene | 2-(5-carboethoxypent-2-cis-enyl)cyclopent-2-en-1-one | dl-16-hydroxy-9-oxo-16-(1-fluorovinyl)-20-methyl-2-nor-5-cis-13-trans prostadienoic acid |
| 49 | 1-trans-tri-n-butylstannyl-4-(1-fluorovinyl)-4-trimethylsiloxy-1-decene | 2-(5-carboethoxypent-2-cis-enyl)cyclopent-2-en-1-one | dl-16-hydroxy-9-oxo-16-(1-fluorovinyl)-20-ethyl-2-nor-5-cis-13-trans prostadienoic acid |
| 50 | 1-trans-tri-n-butylstannyl-4-(1-fluorovinyl)-4-trimethylsiloxy-1-heptene | 2-(6-carboethoxyhex-2-cis-enyl)cyclopent-2-en-1-one | dl-16-hydroxy-9-oxo-16-(1-fluorovinyl)-20-nor-5-cis-13-trans prostadienoic acid |
| 51 | 1-trans-tri-n-butylstannyl-4-(1-fluorovinyl)-4-trimethylsiloxy-1-octene | 2-(6-carboethoxyhex-2-cis-enyl)cyclopent-2-en-1-one | dl-16-hydroxy-9-oxo-16-(1-fluorovinyl)-5-cis-13-trans prostadienoic acid |

| | -continued | |
|---|---|---|
| 52 | 4-trimethylsiloxy-1-octene | 5-cis-13-trans prostadienoic acid |
| | 1-trans-tri-n-butylstannyl-4-(1-fluorovinyl)- | 2-(6-carboethoxyhex-2-cis-enyl)- |
| | 4-trimethylsiloxy-1-nonene | cyclopent-2-en-1-one |
| 53 | 1-trans-tri-n-butylstannyl-4-(1-fluorovinyl)- | 2-(6-carboethoxyhex-2-cis-enyl)- |
| | 4-trimethylsiloxy-1-decene | cyclopent-2-en-1-one |
| | | 20-methyl-5-cis-13-trans prostadienoic acid |
| 54 | 1-trans-tri-n-butylstannyl-4-(1-fluorovinyl)- | 2-(7-carboethoxyhept-2-cis-enyl)- |
| | 4-trimethylsiloxy-1-heptene | cyclopent-2-en-1-one |
| | | 20-ethyl-5-cis-13-trans prostadienoic acid |
| | | dl-16-hydroxy-9-oxo-16-(1-fluorovinyl)- |
| 55 | 1-trans-tri-n-butylstannyl-4-(1-fluorovinyl)- | 2-(7-carboethoxyhept-2-cis-enyl)- |
| | 4-trimethylsiloxy-1-octene | cyclopent-2-en-1-one |
| | | 20-nor-2-homo-5-cis-13-trans prostadienoic acid |
| | | dl-16-hydroxy-9-oxo-16-(1-fluorovinyl)- |
| 56 | 1-trans-tri-n-butylstannyl-4-(1-fluorovinyl)- | 2-(7-carboethoxyhept-2-cis-enyl)- |
| | 4-trimethylsiloxy-1-nonene | cyclopent-2-en-1-one |
| | | 2-homo-5-cis-13-trans prostadienoic acid |
| | | dl-16-hydroxy-9-oxo-16-(1-fluorovinyl)- |
| 57 | 1-trans-tri-n-butylstannyl-4-(1-fluorovinyl)- | 2-(7-carboethoxyhept-2-cis-enyl)- |
| | 4-trimethylsiloxy-1-decene | cyclopent-2-en-1-one |
| | | 20-methyl-2-homo-5-cis-13-trans prostadienoic acid |
| | | dl-16-hydroxy-9-oxo-16-(1-fluorovinyl)- |
| | | 20-ethyl-2-homo-5-cis-13-trans prostadienoic acid |

| EXAMPLE | STARTING PROSTAGLANDIN OF THE PGE SERIES | PRODUCT PROSTAGLANDIN OF THE PGF2a SERIES |
|---|---|---|
| 58 | dl-11a,16-dihydroxy-9-oxo-16-(1-fluorovinyl)-20-nor-2-nor-5-cis-13-trans prostadienoic acid | dl-9a,11a,16-trihydroxy-16-(1-fluorovinyl)-20-nor-2-nor-5-cis-3-trans prostadienoic acid |
| 59 | dl-11a,16-dihydroxy-9-oxo-16-(1-fluorovinyl)-2-nor-5-cis-13-trans prostadienoic acid | dl-9a,11a,16-trihydroxy-16-(1-fluorovinyl)-2-nor-5-cis-13-trans prostadienoic acid |
| 60 | dl-11a,16-dihydroxy-9-oxo-16-(1-fluorovinyl)-20-methyl-2-nor-5-cis-13-trans prostadienoic acid | dl-9a,11a,16-trihydroxy-16-(1-fluorovinyl)-20-methyl-2-nor-5-cis-13-trans prostadienoic acid |
| 61 | dl-11a,16-dihydroxy-9-oxo-16-(1-fluorovinyl)-20-ethyl-2-nor-5-cis-13-trans prostadienoic acid | dl-9a,11a,16-trihydroxy-16-(1-fluorovinyl)-20-ethyl-2-nor-5-cis-13-trans prostadienoic acid |
| 62 | dl-11a,16-dihydroxy-9-oxo-16-(1-fluorovinyl)-20-nor-5-cis-13-trans prostadienoic acid | dl-9a,11a,16-trihydroxy-16-(1-fluorovinyl)-20-nor-5-cis-13-trans prostadienoic acid |
| 63 | dl-11a,16-dihydroxy-9-oxo-16-(1-fluorovinyl)-5-cis-13-trans prostadienoic acid | dl-9a,11a,16-trihydroxy-16-(1-fluorovinyl)-5-cis-13 trans prostadienoic acid |
| 64 | dl-11a,16-dihydroxy-9-oxo-16-(1-fluorovinyl)-20-methyl-5-cis-13-trans prostadienoic acid | dl-9a,11a,16-trihydroxy-16-(1-fluorovinyl)-20-methyl-5-cis-13-trans prostadienoic acid |
| 65 | dl-11a,16-dihydroxy-9-oxo-16-(1-fluorovinyl)-20-ethyl-5-cis-13-trans prostadienoic acid | dl-9a,11a,16-trihydroxy-16-(1-fluorovinyl)-20-ethyl-5-cis-13-trans prostadienoic acid |
| 66 | dl-11a,16-dihydroxy-9-oxo-16-(1-fluorovinyl)-20-nor-2-homo-5-cis-13-trans prostadienoic acid | dl-9a,11a,16-trihydroxy-16-(1-fluorovinyl)-20-nor-2-homo-5-cis-13-trans prostadienoic acid |
| 67 | dl-11a,16-dihydroxy-9-oxo-16-(1-fluorovinyl)-2-homo-5-cis-13-trans prostadienoic acid | dl-9a,11a,16-trihydroxy-16-(1-fluorovinyl)-2-homo-5-cis-13-trans prostadienoic acid |
| 68 | dl-11a,16-dihydroxy-9-oxo-16-(1-fluorovinyl)-20-methyl-2-homo-5-cis-13-trans prostadienoic acid | dl-9a,11a,16-trihydroxy-16-(1-fluorovinyl)-20-methyl-2-homo-5-cis-13-trans prostadienoic acid |
| 69 | dl-11a,16-dihydroxy-9-oxo-16-(1-fluorovinyl)-20-ethyl-2-homo-5-cis-13-trans prostadienoic acid | dl-9a,11a,16-trihydroxy-16-(1-fluorovinyl)-20-ethyl-2-homo-5-cis-13-trans prostadienoic acid |
| 70 | nat-11a,16-dihydroxy-9-oxo-16-(1-fluorovinyl)-5-cis-13-trans prostadienoic acid | nat-9a,11a,16-trihydroxy-16-(1-fluorovinyl)-5-cis-13-trans prostadienoic acid |
| 71 | nat-11a,16-dihydroxy-9-oxo-16-(1-fluorovinyl)-20-methyl-5-cis-13-trans prostadienoic acid | nat-9a,11a,16-trihydroxy-16-(1-fluorovinyl)-20-methyl-5-cis-13-trans prostadienoic acid |
| 72 | nat-11a,16-dihydroxy-9-oxo-16-(1-fluorovinyl)-5-cis-13-trans prostadienoic acid | nat-9a,11a,16-trihydroxy-16-(1-fluorovinyl)-5-cis-13-trans prostadienoic acid |
| 73 | dl-11a,16-dihydroxy-9-oxo-16-(1-fluorovinyl)-20-ethyl-5-cis-13-trans prostadienoic acid | nat-9a,11a,16-trihydroxy-16-(1-fluorovinyl)-20-ethyl-5-cis-13-trans prostadienoic acid |

| EXAMPLE | STARTING PROSTAGLANDIN OF THE PGE SERIES | PRODUCT PROSTAGLANDIN OF THE 11-DEOXY PGF2a SERIES |
|---|---|---|
| 74 | dl-16-hydroxy-9-oxo-16-(1-fluorovinyl)-20-nor-2-nor-5-cis-13-trans prostadienoic acid | dl-9a,16-dihydroxy-16-(1-fluorovinyl)-20-nor-2-nor-5-cis-3-trans prostadienoic acid |
| 75 | dl-16-hydroxy-9-oxo-16-(1-fluorovinyl)-2-nor-5-cis-13-trans prostadienoic acid | dl-9a,16-dihydroxy-16-(1-fluorovinyl)-2-nor-5-cis-13-trans prostadienoic acid |
| 76 | dl-16-hydroxy-9-oxo-16-(1-fluorovinyl)-20-methyl-2-nor-5-cis-13-trans prostadienoic acid | dl-9a,16-dihydroxy-16-(1-fluorovinyl)-20-methyl-2-nor-5-cis-13-trans prostadienoic acid |
| 77 | dl-16-hydroxy-9-oxo-16-(1-fluorovinyl)-20-ethyl-2-nor-5-cis-13-trans prostadienoic acid | dl-9a,16-dihydroxy-16-(1-fluorovinyl)-20-ethyl-2-nor-5-cis-13-trans prostadienoic acid |
| 78 | dl-16-hydroxy-9-oxo-16-(1-fluorovinyl)-20-nor-5-cis-13-trans prostadienoic acid | dl-9a,16-dihydroxy-16-(1-fluorovinyl)-20-nor-5-cis-13-trans prostadienoic acid |
| 79 | dl-16-hydroxy-9-oxo-16-(1-fluorovinyl)-5-cis-13-trans prostadienoic acid | dl-9a,16-dihydroxy-16-(1-fluorovinyl)-5-cis-13-trans prostadienoic acid |
| 80 | dl-16-hydroxy-9-oxo-16-(1-fluorovinyl)-20-methyl-5-cis-13-trans prostadienoic acid | dl-9a,16-dihydroxy-16-(1-fluorovinyl)-20-methyl-5-cis-13-trans prostadienoic acid |
| 81 | dl-16-hydroxy-9-oxo-16-(1-fluorovinyl)-20-ethyl-5-cis-13-trans prostadienoic acid | dl-9a,16-dihydroxy-16-(1-fluorovinyl)-20-ethyl-5-cis-13-trans prostadienoic acid |
| 82 | dl-16-hydroxy-9-oxo-16-(1-fluorovinyl)-20-nor-2-homo-5-cis-13-trans prostadienoic acid | dl-9a,16-dihydroxy-16-(1-fluorovinyl)-20-nor-2-homo-5-cis-13-trans prostadienoic acid |
| 83 | dl-16-hydroxy-9-oxo-16-(1-fluorovinyl)-2-homo-5-cis-13-trans prostadienoic acid | dl-9a,16-dihydroxy-16-(1-fluorovinyl)-2-homo-5-cis-13-trans prostadienoic acid |
| 84 | dl-16-hydroxy-9-oxo-16-(1-fluorovinyl)-20-methyl-2-homo-5-cis-13-trans prostadienoic acid | dl-9a,16-dihydroxy-16-(1-fluorovinyl)-20-methyl-2-homo-5-cis-13-trans prostadienoic acid |
| 85 | dl-16-hydroxy-9-oxo-16-(1-fluorovinyl)-20-ethyl-2-homo-5-cis-13-trans prostadienoic acid | dl-9a,16-dihydroxy-16-(1-fluorovinyl)-20-ethyl-2-homo-5-cis-13-trans prostadienoic acid |

| EXAMPLE | STARTING PROSTAGLANDIN OF THE PGE SERIES | PRODUCT PROSTAGLANDIN OF THE PGF2B SERIES |
|---|---|---|
| 86 | dl-11a,16-trihydroxy-16-(1-fluorovinyl)-20-nor-2-nor-5-cis-13-trans prostadienoic acid | dl-9B,11a,16-trihydroxy-16-(1-fluorovinyl)-20-nor-2-nor-5-cis-13-trans prostadienoic acid |
| 87 | dl-11a,16-trihydroxy-16-(1-fluorovinyl)-2-nor-5-cis-13-trans prostadienoic acid | dl-9B,11a,16-trihydroxy-16-(1-fluorovinyl)-2-nor-5-cis-13-trans prostadienoic acid |
| 88 | dl-11a,16-trihydroxy-16-(1-fluorovinyl)-20-methyl-2-nor-5-cis-13-trans prostadienoic acid | dl-9B,11a,16-trihydroxy-16-(1-fluorovinyl)-20-methyl-2-nor-5-cis-13-trans prostadienoic acid |
| 89 | dl-11a,16-trihydroxy-16-(1-fluorovinyl)-20-ethyl-2-nor-5-cis-13-trans prostadienoic acid | dl-9B,11a,16-trihydroxy-16-(1-fluorovinyl)-20-ethyl-2-nor-5-cis-13-trans prostadienoic acid |
| 90 | dl-11a,16-dihydroxy-9-oxo-16-(1-fluorovinyl)-20-nor-5-cis-13-trans prostadienoic acid | dl-9B,11a,16-trihydroxy-16-(1-fluorovinyl)-20-nor-5-cis-13-trans prostadienoic acid |
| 91 | dl-11a,16-trihydroxy-16-(1-fluorovinyl)-5-cis-13-trans prostadienoic acid | dl-9B,11a,16-trihydroxy-16-(1-fluorovinyl)-5-cis-13-trans prostadienoic acid |

-continued

| | STARTING PROSTAGLANDIN OF THE PGE SERIES | PRODUCT PROSTAGLANDIN OF THE 11-DEOXY PGF2B SERIES |
|---|---|---|
| 92 | dl-11a,16-dihydroxy-9-oxo-16-(1-fluorovinyl)-20-methyl-5-cis-13-trans prostadienoic acid | dl-9B,11a,16-trihydroxy-16-(1-fluorovinyl)-20-methyl-5-cis-13-trans prostadienoic acid |
| 93 | dl-11a,16-dihydroxy-9-oxo-16-(1-fluorovinyl)-20-ethyl-5-cis-13-trans prostadienoic acid | dl-9B,11a,16-trihydroxy-16-(1-fluorovinyl)-20-ethyl-5-cis-13-trans prostadienoic acid |
| 94 | dl-11a,16-dihydroxy-9-oxo-16-(1-fluorovinyl)-20-nor-2-homo-5-cis-13-trans prostadienoic acid | dl-9B,11a,16-trihydroxy-16-(1-fluorovinyl)-20-nor-2-homo-5-cis-13-trans prostadienoic acid |
| 95 | dl-11a,16-dihydroxy-9-oxo-16-(1-fluorovinyl)-2-homo-5-cis-13-trans prostadienoic acid | dl-9B,11a,16-trihydroxy-16-(1-fluorovinyl)-2-homo-5-cis-13-trans prostadienoic acid |
| 96 | dl-11a,16-dihydroxy-9-oxo-16-(1-fluorovinyl)-20-methyl-2-homo-5-cis-13-trans prostadienoic acid | dl-9B,11a,16-trihydroxy-16-(1-fluorovinyl)-20-methyl-2-homo-5-cis-13-trans prostadienoic acid |
| 97 | dl-11a,16-dihydroxy-9-oxo-16-(1-fluorovinyl)-20-ethyl-2-homo-5-cis-13-trans prostadienoic acid | dl-9B,11a,16-trihydroxy-16-(1-fluorovinyl)-20-ethyl-2-homo-5-cis-13-trans prostadienoic acid |
| 98 | nat-11a,16-dihydroxy-9-oxo-16-(1-fluorovinyl)-20-nor-5-cis-13-trans prostadienoic acid | nat-9B,11a,16-trihydroxy-16-(1-fluorovinyl)-20-nor-5-cis-13-trans prostadienoic acid |
| 99 | nat-11a,16-dihydroxy-9-oxo-16-(1-fluorovinyl)-5-cis-13-trans prostadienoic acid | nat-9B,11a,16-trihydroxy-16-(1-fluorovinyl)-5-cis-13-trans prostadienoic acid |
| 100 | nat-11a,16-dihydroxy-9-oxo-16-(1-fluorovinyl)-20-methyl-5-cis-13-trans prostadienoic acid | nat-9B,11a,16-trihydroxy-16-(1-fluorovinyl)-20-methyl-5-cis-13-trans prostadienoic acid |
| 101 | nat-11a,16-dihydroxy-9-oxo-16-(1-fluorovinyl)-20-ethyl-5-cis-13-trans prostadienoic acid | nat-9B,11a,16-trihydroxy-16-(1-fluorovinyl)-20-ethyl-5-cis-13-trans prostadienoic acid |

| EXAMPLE | STARTING PROSTAGLANDIN OF THE PGE SERIES | PRODUCT PROSTAGLANDIN OF THE 11-DEOXY PGF2B SERIES |
|---|---|---|
| 102 | dl-16-hydroxy-9-oxo-16-(1-fluorovinyl)-20-nor-2-nor-5-cis-13-trans prostadienoic acid | dl-9B,16-dihydroxy-16-(1-fluorovinyl)-20-nor-2-nor-5-cis-13-trans prostadienoic acid |
| 103 | dl-16-hydroxy-9-oxo-16-(1-fluorovinyl)-2-nor-5-cis-13-trans prostadienoic acid | dl-9B,16-dihydroxy-16-(1-fluorovinyl)-2-nor-5-cis-13-trans prostadienoic acid |
| 104 | dl-16-hydroxy-9-oxo-16-(1-fluorovinyl)-20-methyl-2-nor-5-cis-13-trans prostadienoic acid | dl-9B,16-dihydroxy-16-(1-fluorovinyl)-20-methyl-2-nor-5-cis-13-trans prostadienoic acid |
| 105 | dl-16-hydroxy-9-oxo-16-(1-fluorovinyl)-20-ethyl-2-nor-5-cis-13-trans prostadienoic acid | dl-9B,16-dihydroxy-16-(1-fluorovinyl)-20-ethyl-2-nor-5-cis-13-trans prostadienoic acid |
| 106 | dl-16-hydroxy-9-oxo-16-(1-fluorovinyl)-20-nor-5-cis-13-trans prostadienoic acid | dl-9B,16-dihydroxy-16-(1-fluorovinyl)-20-nor-5-cis-13-trans prostadienoic acid |
| 107 | dl-16-hydroxy-9-oxo-16-(1-fluorovinyl)-5-cis-13-trans prostadienoic acid | dl-9B,16-dihydroxy-16-(1-fluorovinyl)-5-cis-13-trans prostadienoic acid |
| 108 | dl-16-hydroxy-9-oxo-16-(1-fluorovinyl)-20-methyl-5-cis-13-trans prostadienoic acid | dl-9B,16-dihydroxy-16-(1-fluorovinyl)-20-methyl-5-cis-13-trans prostadienoic acid |
| 109 | dl-16-hydroxy-9-oxo-16-(1-fluorovinyl)-20-ethyl-5-cis-13-trans prostadienoic acid | dl-9B,16-dihydroxy-16-(1-fluorovinyl)-20-ethyl-5-cis-13-trans prostadienoic acid |
| 110 | dl-16-hydroxy-9-oxo-16-(1-fluorovinyl)-20-nor-2-homo-5-cis-13-trans prostadienoic acid | dl-9B,16-dihydroxy-16-(1-fluorovinyl)-20-nor-2-homo-5-cis-13-trans prostadienoic acid |
| 111 | dl-16-hydroxy-9-oxo-16-(1-fluorovinyl)-2-homo-5-cis-13-trans prostadienoic acid | dl-9B,16-dihydroxy-16-(1-fluorovinyl)-2-homo-5-cis-13-trans prostadienoic acid |
| 112 | dl-16-hydroxy-9-oxo-16-(1-fluorovinyl)-20-methyl-2-homo-5-cis-13-trans prostadienoic acid | dl-9B,16-dihydroxy-16-(1-fluorovinyl)-20-methyl-2-homo-5-cis-13-trans prostadienoic acid |
| 113 | dl-16-hydroxy-9-oxo-16-(1-fluorovinyl)-20-ethyl-2-homo-5-cis-13-trans prostadienoic acid | dl-9B,16-dihydroxy-16-(1-fluorovinyl)-20-ethyl-2-homo-5-cis-13-trans prostadienoic acid |

| EXAMPLE | VINYL TIN | CYCLOPENTENONE | PRODUCT PROSTAGLANDIN OF THE PGE1 SERIES |
|---|---|---|---|
| 114 | 1-trans-tri-n-butylstannyl-4-(1-fluorovinyl)-4-trimethylsilyloxy-1-heptene | 2-(5-carbotrimethylsiloxycyclopent-2-en-1-one | dl-11a,16-dihydroxy-9-oxo-16-(1-fluorovinyl)-20-nor-2-nor-13-trans prostenoic acid |
| 115 | 1-trans-tri-n-butylstannyl-4-(1-fluorovinyl)-4-trimethylsilyloxy-1-pentene | 4-trimethylsiloxycyclopent-2-en-1-one | dl-11a,16-dihydroxy-9-oxo-16-(1-fluorovinyl)-2-nor-13-trans prostenoic acid |
| 116 | 1-trans-tri-n-butylstannyl-4-(1-fluorovinyl)-4-trimethylsilyloxy-1-octene | 2-(5-carbotrimethylsiloxycyclopent-2-en-1-one | 2-nor-13-trans prostenoic acid |
| 117 | 1-trans-tri-n-butylstannyl-4-(1-fluorovinyl)-4-trimethylsilyloxy-1-nonene | 4-trimethylsiloxycyclopent-2-en-1-one | dl-11a,16-dihydroxy-9-oxo-16-(1-fluorovinyl)-20-methyl-2-nor-13-trans prostenoic acid |
| 118 | 1-trans-tri-n-butylstannyl-4-(1-fluorovinyl)-4-trimethylsilyloxy-1-decene | 2-(5-carbotrimethylsiloxycyclopent-2-en-1-one | dl-11a,16-dihydroxy-9-oxo-16-(1-fluorovinyl)-20-ethyl-2-nor-13-trans prostenoic acid |
| 119 | 1-trans-tri-n-butylstannyl-4-(1-fluorovinyl)-4-trimethylsilyloxy-1-heptene | 2-(6-carbotrimethylsiloxycyclopent-2-en-1-one | dl-11a,16-dihydroxy-9-oxo-16-(1-fluorovinyl)-20-nor-13-trans prostenoic acid |
| 120 | 1-trans-tri-n-butylstannyl-4-(1-fluorovinyl)-4-trimethylsilyloxy-1-octene | 2-(6-carbotrimethylsiloxycyclopent-2-en-1-one | dl-11a,16-dihydroxy-9-oxo-16-(1-fluorovinyl)-13-trans prostenoic acid |
| 121 | 1-trans-tri-n-butylstannyl-4-(1-fluorovinyl)-4-trimethylsilyloxy-1-nonene | 4-trimethylsiloxycyclopent-2-en-1-one | dl-11a,16-dihydroxy-9-oxo-16-(1-fluorovinyl)-20-methyl-13-trans prostenoic acid |
| 122 | 1-trans-tri-n-butylstannyl-4-(1-fluorovinyl)-4-trimethylsilyloxy-1-decene | 2-(7-carbotrimethylsiloxycyclopent-2-en-1-one | dl-11a,16-dihydroxy-9-oxo-16-(1-fluorovinyl)-20-ethyl-13-trans prostenoic acid |
| 123 | 1-trans-tri-n-butylstannyl-4-(1-fluorovinyl)-4-trimethylsilyloxy-1-heptene | 4-trimethylsiloxycyclopent-2-en-1-one | dl-11a,16-dihydroxy-9-oxo-16-(1-fluorovinyl)-20-nor-2-homo-13-trans prostenoic acid |
| 124 | 1-trans-tri-n-butylstannyl-4-(1-fluorovinyl)-4-trimethylsilyloxy-1-octene | 2-(7-carbotrimethylsiloxycyclopent-2-en-1-one | dl-11a,16-dihydroxy-9-oxo-16-(1-fluorovinyl)-2-homo-13-trans prostenoic acid |
| 125 | 1-trans-tri-n-butylstannyl-4-(1-fluorovinyl)-4-trimethylsilyloxy-1-nonene | 2-(7-carbotrimethylsiloxycyclopent-2-en-1-one | dl-11a,16-dihydroxy-9-oxo-16-(1-fluorovinyl)-20-methyl-2-homo-13-trans prostenoic acid |
| 126 | 1-trans-tri-n-butylstannyl-4-(1-fluorovinyl)-4-trimethylsilyloxy-1-decene | 2-(6-carbotrimethylsiloxycyclopent-2-en-1-one | dl-11a,16-dihydroxy-9-oxo-16-(1-fluorovinyl)-20-ethyl-2-homo-13-trans prostenoic acid |
| 127 | 1-trans-tri-n-butylstannyl-4-(1-fluorovinyl)-4-trimethylsilyloxy-1-heptene | 4R-trimethylsiloxycyclopent-2-en-1-one | nat-11a,16-dihydroxy-9-oxo-16-(1-fluorovinyl)-20-nor-13-trans prostenoic acid |

| EXAMPLE | VINYL TIN | CYCLOPENTENONE | PRODUCT PROSTAGLANDIN OF THE 11-DEOXY PGE1 SERIES |
|---|---|---|---|
| 128 | 4-trimethylsiloxy-1-octene | 4R-trimethylsiloxycyclopent-2-en-1-one | 13-trans prostenoic acid |
| | 1-trans-tri-n-butylstannyl-4-(1-fluorovinyl)- | 2-(6-carbotrimethylsiloxyhexyl)- | nat-11a,16-dihydroxy-9-oxo-16-(1-fluorovinyl)- |
| | 4-trimethylsiloxy-1-nonene | 4R-trimethylsiloxycyclopent-2-en-1-one | 20-methyl-13-trans prostenoic acid |
| 129 | 1-trans-tri-n-butylstannyl-4-(1-fluorovinyl)- | 2-(6-carbotrimethylsiloxyhexyl)- | nat-11a,16-dihydroxy-9-oxo-16-(1-fluorovinyl)- |
| | 4-trimethylsiloxy-1-decene | 4R-trimethylsiloxycyclopent-2-en-1-one | 20-ethyl-13-trans prostenoic acid |

| EXAMPLE | VINYL TIN | CYCLOPENTENONE | PRODUCT PROSTAGLANDIN OF THE 11-DEOXY PGE1 SERIES |
|---|---|---|---|
| 130 | 1-trans-tri-n-butylstannyl-4-(1-fluorovinyl)-4-trimethylsiloxy-1-heptene | 2-(5-carboethoxypentyl)cyclopent-2-en-1-one | dl-16-hydroxy-9-oxo-16-(1-fluorovinyl)-20-nor-2-nor-13-trans prostenoic acid |
| 131 | 1-trans-tri-n-butylstannyl-4-(1-fluorovinyl)-4-trimethylsiloxy-1-octene | 2-(5-carboethoxypentyl)cyclopent-2-en-1-one | dl-16-hydroxy-9-oxo-16-(1-fluorovinyl)-2-nor-13-trans prostenoic acid |
| 132 | 1-trans-tri-n-butylstannyl-4-(1-fluorovinyl)-4-trimethylsiloxy-1-nonene | 2-(5-carboethoxypentyl)cyclopent-2-en-1-one | dl-16-hydroxy-9-oxo-16-(1-fluorovinyl)-20-methyl-2-nor-13-trans prostenoic acid |
| 133 | 1-trans-tri-n-butylstannyl-4-(1-fluorovinyl)-4-trimethylsiloxy-1-decene | 2-(5-carboethoxypentyl)cyclopent-2-en-1-one | dl-16-hydroxy-9-oxo-16-(1-fluorovinyl)-20-ethyl-2-nor-13-trans prostenoic acid |
| 134 | 1-trans-tri-n-butylstannyl-4-(1-fluorovinyl)-4-trimethylsiloxy-1-heptene | 2-(6-carboethoxyhexyl)cyclopent-2-en-1-one | dl-16-hydroxy-9-oxo-16-(1-fluorovinyl)-20-nor-13-trans prostenoic acid |
| 135 | 1-trans-tri-n-butylstannyl-4-(1-fluorovinyl)-4-trimethylsiloxy-1-octene | 2-(6-carboethoxyhexyl)cyclopent-2-en-1-one | dl-16-hydroxy-9-oxo-16-(1-fluorovinyl)-13-trans prostenoic acid |
| 136 | 1-trans-tri-n-butylstannyl-4-(1-fluorovinyl)-4-trimethylsiloxy-1-nonene | 2-(6-carboethoxyhexyl)cyclopent-2-en-1-one | dl-16-hydroxy-9-oxo-16-(1-fluorovinyl)-20-methyl-13-trans prostenoic acid |
| 137 | 1-trans-tri-n-butylstannyl-4-(1-fluorovinyl)-4-trimethylsiloxy-1-decene | 2-(6-carboethoxyhexyl)cyclopent-2-en-1-one | dl-16-hydroxy-9-oxo-16-(1-fluorovinyl)-20-ethyl-13-trans prostenoic acid |
| 138 | 1-trans-tri-n-butylstannyl-4-(1-fluorovinyl)-4-trimethylsiloxy-1-heptene | 2-(7-carboethoxyheptyl)cyclopent-2-en-1-one | dl-16-hydroxy-9-oxo-16-(1-fluorovinyl)-20-nor-2-homo-13-trans prostenoic acid |
| 139 | 1-trans-tri-n-butylstannyl-4-(1-fluorovinyl)-4-trimethylsiloxy-1-octene | 2-(7-carboethoxyheptyl)cyclopent-2-en-1-one | dl-16-hydroxy-9-oxo-16-(1-fluorovinyl)-2-homo-13-trans prostenoic acid |
| 140 | 1-trans-tri-n-butylstannyl-4-(1-fluorovinyl)-4-trimethylsiloxy-1-nonene | 2-(7-carboethoxyheptyl)cyclopent-2-en-1-one | dl-16-hydroxy-9-oxo-16-(1-fluorovinyl)-20-methyl-2-homo-13-trans prostenoic acid |
| 141 | 1-trans-tri-n-butylstannyl-4-(1-fluorovinyl)-4-trimethylsiloxy-1-decene | 2-(7-carboethoxyheptyl)cyclopent-2-en-1-one | dl-16-hydroxy-9-oxo-16-(1-fluorovinyl)-20-ethyl-2-homo-13-trans prostenoic acid |

| EXAMPLE | VINYL TIN | CYCLOPENTENONE | PRODUCT PROSTAGLANDIN OF THE PGE1 SERIES |
|---|---|---|---|
| 142 | 1-trans-tri-n-butylstannyl-4-(1-fluorovinyl)-4-trimethylsiloxy-1-heptene | 2-(5-carbotrimethylsilyloxypentyl)-4-trimethylsiloxycyclopent-2-en-1-one | dl-11a,16-dihydroxy-9-oxo-16-(1-fluorovinyl)-20-nor-2-nor-13-trans prostenoic acid |
| 143 | 1-trans-tri-n-butylstannyl-4-(1-fluorovinyl)-4-trimethylsiloxy-1-octene | 2-(5-carbotrimethylsilyloxypentyl)-4-trimethylsiloxycyclopent-2-en-1-one | dl-11a,16-dihydroxy-9-oxo-16-(1-fluorovinyl)-2-nor-13-trans prostenoic acid |
| 144 | 1-trans-tri-n-butylstannyl-4-(1-fluorovinyl)-4-trimethylsiloxy-1-nonene | 2-(5-carbotrimethylsilyloxypentyl)-4-trimethylsiloxycyclopent-2-en-1-one | dl-11a,16-dihydroxy-9-oxo-16-(1-fluorovinyl)-20-methyl-2-nor-13-trans prostenoic acid |
| 145 | 1-trans-tri-n-butylstannyl-4-(1-fluorovinyl)-4-trimethylsiloxy-1-decene | 2-(5-carbotrimethylsilyloxypentyl)-4-trimethylsiloxycyclopent-2-en-1-one | dl-11a,16-dihydroxy-9-oxo-16-(1-fluorovinyl)-20-ethyl-2-nor-13-trans prostenoic acid |
| 146 | 1-trans-tri-n-butylstannyl-4-(1-fluorovinyl)-4-trimethylsiloxy-1-heptene | 2-(6-carbotrimethylsilyloxyhexyl)-4-trimethylsiloxycyclopent-2-en-1-one | dl-11a,16-dihydroxy-9-oxo-16-(1-fluorovinyl)-20-nor-13-trans prostenoic acid |
| 147 | 1-trans-tri-n-butylstannyl-4-(1-fluorovinyl)-4-trimethylsiloxy-1-octene | 2-(6-carbotrimethylsilyloxyhexyl)-4-trimethylsiloxycyclopent-2-en-1-one | dl-11a,16-dihydroxy-9-oxo-16-(1-fluorovinyl)-13-trans prostenoic acid |
| 148 | 1-trans-tri-n-butylstannyl-4-(1-fluorovinyl)-4-trimethylsiloxy-1-nonene | 2-(6-carbotrimethylsilyloxyhexyl)-4-trimethylsiloxycyclopent-2-en-1-one | dl-11a,16-dihydroxy-9-oxo-16-(1-fluorovinyl)-20-methyl-13-trans prostenoic acid |
| 149 | 1-trans-tri-n-butylstannyl-4-(1-fluorovinyl)-4-trimethylsiloxy-1-decene | 2-(6-carbotrimethylsilyloxyhexyl)-4-trimethylsiloxycyclopent-2-en-1-one | dl-11a,16-dihydroxy-9-oxo-16-(1-fluorovinyl)-20-ethyl-13-trans prostenoic acid |
| 150 | 1-trans-tri-n-butylstannyl-4-(1-fluorovinyl)-4-trimethylsiloxy-1-heptene | 2-(7-carbotrimethylsilyloxyheptyl)-4-trimethylsiloxycyclopent-2-en-1-one | dl-11a,16-dihydroxy-9-oxo-16-(1-fluorovinyl)-20-nor-2-homo-13-trans prostenoic acid |
| 151 | 1-trans-tri-n-butylstannyl-4-(1-fluorovinyl)-4-trimethylsiloxy-1-octene | 2-(7-carbotrimethylsilyloxyheptyl)-4-trimethylsiloxycyclopent-2-en-1-one | dl-11a,16-dihydroxy-9-oxo-16-(1-fluorovinyl)-2-homo-13-trans prostenoic acid |

| EXAMPLE | STARTING PROSTAGLANDIN OF THE PGE SERIES | VINYL TIN | CYCLOPENTENONE | PRODUCT PROSTAGLANDIN OF THE 11-DEOXY PGE1 SERIES |
|---|---|---|---|---|
| 152 | | 1-trans-tri-n-butylstannyl-4-(1-fluorovinyl)-4-trimethylsiloxy-1-heptene | 2-(7-carbotrimethylsilyloxyheptyl)-4-trimethylsiloxycyclopent-2-en-1-one | dl-11a,16-dihydroxy-9-oxo-16-(1-fluorovinyl)-20-methyl-2-homo-13-trans prostenoic acid |
| 153 | | 1-trans-tri-n-butylstannyl-4-(1-fluorovinyl)-4-trimethylsiloxy-1-nonene | 2-(7-carbotrimethylsilyloxyheptyl)-4-trimethylsiloxycyclopent-2-en-1-one | dl-11a,16-dihydroxy-9-oxo-16-(1-fluorovinyl)-20-ethyl-2-homo-13-trans prostenoic acid |
| 154 | | 1-trans-tri-n-butylstannyl-4-(1-fluorovinyl)-4-trimethylsiloxy-1-decene | 2-(6-carbotrimethylsilyloxyhexyl)-4-trimethylsiloxycyclopent-2-en-1-one | nat-11a,16-dihydroxy-9-oxo-16-(1-fluorovinyl)-13-trans prostenoic acid |
| 155 | | 1-trans-tri-n-butylstannyl-4-(1-fluorovinyl)-4-trimethylsiloxy-1-heptene | 4R-trimethylsiloxycyclopent-2-en-1-one | nat-11a,16-dihydroxy-9-oxo-16-(1-fluorovinyl)-13-trans prostenoic acid |
| 156 | | 1-trans-tri-n-butylstannyl-4-(1-fluorovinyl)-4-trimethylsiloxy-1-octene | 2-(6-carbotrimethylsilyloxyhexyl)-4R-trimethylsiloxycyclopent-2-en-1-one | nat-11a,16-dihydroxy-9-oxo-16-(1-fluorovinyl)-20-methyl-13-trans prostenoic acid |
| 157 | | 1-trans-tri-n-butylstannyl-4-(1-fluorovinyl)-4-trimethylsiloxy-1-nonene | 2-(6-carbotrimethylsilyloxyhexyl)-4R-trimethylsiloxycyclopent-2-en-1-one | nat-11a,16-dihydroxy-9-oxo-16-(1-fluorovinyl)-20-ethyl-13-trans prostenoic acid |

| EXAMPLE | VINYL TIN | CYCLOPENTENONE | PRODUCT PROSTAGLANDIN OF THE 11-DEOXY PGE1 SERIES |
|---|---|---|---|
| 158 | 1-trans-tri-n-butylstannyl-4-(1-fluorovinyl)-4-trimethylsiloxy-1-heptene | 2-(5-carboethoxypentyl)cyclopent-2-en-1-one | dl-16-hydroxy-9-oxo-16-(1-fluorovinyl)-20-nor-2-nor-13-trans prostenoic acid |
| 159 | 1-trans-tri-n-butylstannyl-4-(1-fluorovinyl)-4-trimethylsiloxy-1-heptene | 2-(5-carboethoxypentyl)cyclopent-2-en-1-one | dl-16-hydroxy-9-oxo-16-(1-fluorovinyl)-2-nor-13-trans prostenoic acid |
| 160 | 1-trans-tri-n-butylstannyl-4-(1-fluorovinyl)-4-trimethylsiloxy-1-octene | 2-(5-carboethoxypentyl)cyclopent-2-en-1-one | dl-16-hydroxy-9-oxo-16-(1-fluorovinyl)-20-methyl-2-nor-13-trans prostenoic acid |
| 161 | 1-trans-tri-n-butylstannyl-4-(1-fluorovinyl)-4-trimethylsiloxy-1-nonene | 2-(5-carboethoxypentyl)cyclopent-2-en-1-one | dl-16-hydroxy-9-oxo-16-(1-fluorovinyl)-20-ethyl-2-nor-13-trans prostenoic acid |
| 162 | 1-trans-tri-n-butylstannyl-4-(1-fluorovinyl)-4-trimethylsiloxy-1-decene | 2-(6-carboethoxyhexyl)cyclopent-2-en-1-one | dl-16-hydroxy-9-oxo-16-(1-fluorovinyl)-20-nor-13-trans prostenoic acid |
| 163 | 1-trans-tri-n-butylstannyl-4-(1-fluorovinyl)-4-trimethylsiloxy-1-heptene | 2-(6-carboethoxyhexyl)cyclopent-2-en-1-one | 13-trans prostenoic acid |
| 164 | 1-trans-tri-n-butylstannyl-4-(1-fluorovinyl)-4-trimethylsiloxy-1-octene | 2-(6-carboethoxyhexyl)cyclopent-2-en-1-one | dl-16-hydroxy-9-oxo-16-(1-fluorovinyl)-20-methyl-13-trans prostenoic acid |
| 165 | 1-trans-tri-n-butylstannyl-4-(1-fluorovinyl)-4-trimethylsiloxy-1-nonene | 2-(6-carboethoxyhexyl)cyclopent-2-en-1-one | 20-ethyl-13-trans prostenoic acid |
| 166 | 1-trans-tri-n-butylstannyl-4-(1-fluorovinyl)-4-trimethylsiloxy-1-heptene | 2-(7-carboethoxyheptyl)cyclopent-2-en-1-one | dl-16-hydroxy-9-oxo-16-(1-fluorovinyl)-20-nor-2-homo-13-trans prostenoic acid |
| 167 | 1-trans-tri-n-butylstannyl-4-(1-fluorovinyl)-4-trimethylsiloxy-1-octene | 2-(7-carboethoxyheptyl)cyclopent-2-en-1-one | 2-homo-13-trans prostenoic acid |
| 168 | 1-trans-tri-n-butylstannyl-4-(1-fluorovinyl)-4-trimethylsiloxy-1-nonene | 2-(7-carboethoxyheptyl)cyclopent-2-en-1-one | dl-16-hydroxy-9-oxo-16-(1-fluorovinyl)-20-methyl-2-homo-13-trans prostenoic acid |
| 169 | 1-trans-tri-n-butylstannyl-4-(1-fluorovinyl)-4-trimethylsiloxy-1-decene | 2-(7-carboethoxyheptyl)cyclopent-2-en-1-one | 20-ethyl-2-homo-13-trans prostenoic acid |

| EXAMPLE | STARTING PROSTAGLANDIN OF THE PGE SERIES | PRODUCT PROSTAGLANDIN OF THE PGF1a SERIES |
|---|---|---|
| 170 | dl-11a,16-dihydroxy-9-oxo-16-(1-fluorovinyl)-20-nor-2-nor-13-trans prostenoic acid | dl-9a,11a,16-trihydroxy-16-(1-fluorovinyl)-20-nor-2-nor-13-trans prostenoic acid |
| 171 | dl-11a,16-dihydroxy-9-oxo-16-(1-fluorovinyl)-2-nor-13-trans prostenoic acid | dl-9a,11a,16-trihydroxy-16-(1-fluorovinyl)-2-nor-13-trans prostenoic acid |
| 172 | dl-11a,16-dihydroxy-9-oxo-16-(1-fluorovinyl)-20-methyl-2-nor-13-trans prostenoic acid | dl-9a,11a,16-trihydroxy-16-(1-fluorovinyl)-20-methyl-2-nor-13-trans prostenoic acid |
| 173 | dl-11a,16-dihydroxy-9-oxo-16-(1-fluorovinyl)-20-ethyl-2-nor-13-trans prostenoic acid | dl-9a,11a,16-trihydroxy-16-(1-fluorovinyl)-20-ethyl-2-nor-13-trans prostenoic acid |
| 174 | dl-11a,16-dihydroxy-9-oxo-16-(1-fluorovinyl)-20-nor-13-trans prostenoic acid | dl-9a,11a,16-trihydroxy-16-(1-fluorovinyl)-20-nor-13-trans prostenoic acid |
| 175 | dl-11a,16-dihydroxy-9-oxo-16-(1-fluorovinyl)-13-trans prostenoic acid | dl-9a,11a,16-trihydroxy-16-(1-fluorovinyl)-13-trans prostenoic acid |
| 176 | dl-11a,16-dihydroxy-9-oxo-16-(1-fluorovinyl)-20-methyl-13-trans prostenoic acid | dl-9a,11a,16-trihydroxy-16-(1-fluorovinyl)-20-methyl-13-trans prostenoic acid |
| 177 | dl-11a,16-dihydroxy-9-oxo-16-(1-fluorovinyl)-20-ethyl-13-trans prostenoic acid | dl-9a,11a,16-trihydroxy-16-(1-fluorovinyl)-20-ethyl-13-trans prostenoic acid |
| 178 | dl-11a,16-dihydroxy-9-oxo-16-(1-fluorovinyl)-20-nor-2-homo-13-trans prostenoic acid | dl-9a,11a,16-trihydroxy-16-(1-fluorovinyl)-20-nor-2-homo-13-trans prostenoic acid |
| 179 | dl-11a,16-dihydroxy-9-oxo-16-(1-fluorovinyl)-2-homo-13-trans prostenoic acid | dl-9a,11a,16-trihydroxy-16-(1-fluorovinyl)-2-homo-13-trans prostenoic acid |
| 180 | dl-11a,16-dihydroxy-9-oxo-16-(1-fluorovinyl)-20-methyl-2-homo-13-trans prostenoic acid | dl-9a,11a,16-trihydroxy-16-(1-fluorovinyl)-20-methyl-2-homo-13-trans prostenoic acid |
| 181 | dl-11a,16-dihydroxy-9-oxo-16-(1-fluorovinyl)-20-ethyl-2-homo-13-trans prostenoic acid | dl-9a,11a,16-trihydroxy-16-(1-fluorovinyl)-20-ethyl-2-homo-13-trans prostenoic acid |
| 182 | nat-11a,16-dihydroxy-9-oxo-16-(1-fluorovinyl)-20-nor-13-trans prostenoic acid | nat-9a,11a,16-trihydroxy-16-(1-fluorovinyl)-20-nor-13-trans prostenoic acid |

-continued

| EXAMPLE | STARTING PROSTAGLANDIN OF THE PGE SERIES | PRODUCT PROSTAGLANDIN OF THE 11-DEOXY PGF1α SERIES |
|---|---|---|
| 183 | nat-11a,16-dihydroxy-9-oxo-16-(1-fluorovinyl)-13-trans prostenoic acid | nat-9a,11a,16-trihydroxy-16-(1-fluorovinyl)-13-trans prostenoic acid |
| 184 | nat-11a,16-dihydroxy-9-oxo-16-(1-fluorovinyl)-20-methyl-13-trans prostenoic acid | nat-9a,11a,16-trihydroxy-16-(1-fluorovinyl)-20-methyl-13-trans prostenoic acid |
| 185 | nat-11a,16-dihydroxy-9-oxo-16-(1-fluorovinyl)-20-ethyl-13-trans prostenoic acid | nat-9a,11a,16-trihydroxy-16-(1-fluorovinyl)-20-ethyl-13-trans prostenoic acid |

| EXAMPLE | STARTING PROSTAGLANDIN OF THE PGE SERIES | PRODUCT PROSTAGLANDIN OF THE 11-DEOXY PGF1α SERIES |
|---|---|---|
| 186 | dl-16-hydroxy-9-oxo-16-(1-fluorovinyl)-20-nor-2-nor-13-trans prostenoic acid | dl-9a,16-dihydroxy-16-(1-fluorovinyl)-20-nor-2-nor-13-trans prostenoic acid |
| 187 | dl-16-hydroxy-9-oxo-16-(1-fluorovinyl)-2-nor-13-trans prostenoic acid | dl-9a,16-dihydroxy-16-(1-fluorovinyl)-2-nor-13-trans prostenoic acid |
| 188 | dl-16-hydroxy-9-oxo-16-(1-fluorovinyl)-20-methyl-2-nor-13-trans prostenoic acid | dl-9a,16-dihydroxy-16-(1-fluorovinyl)-20-methyl-2-nor-13-trans prostenoic acid |
| 189 | dl-16-hydroxy-9-oxo-16-(1-fluorovinyl)-20-ethyl-2-nor-13-trans prostenoic acid | dl-9a,16-dihydroxy-16-(1-fluorovinyl)-20-ethyl-2-nor-13-trans prostenoic acid |
| 190 | dl-16-hydroxy-9-oxo-16-(1-fluorovinyl)-20-nor-13-trans prostenoic acid | dl-9a,16-dihydroxy-16-(1-fluorovinyl)-20-nor-13-trans prostenoic acid |
| 191 | dl-16-hydroxy-9-oxo-16-(1-fluorovinyl)-13-trans prostenoic acid | dl-9a,16-dihydroxy-16-(1-fluorovinyl)-13-trans prostenoic acid |
| 192 | dl-16-hydroxy-9-oxo-16-(1-fluorovinyl)-20-methyl-13-trans prostenoic acid | dl-9a,16-dihydroxy-16-(1-fluorovinyl)-20-methyl-13-trans prostenoic acid |
| 193 | dl-16-hydroxy-9-oxo-16-(1-fluorovinyl)-20-ethyl-13-trans prostenoic acid | dl-9a,16-dihydroxy-16-(1-fluorovinyl)-20-ethyl-13-trans prostenoic acid |
| 194 | dl-16-hydroxy-9-oxo-16-(1-fluorovinyl)-20-nor-2-homo-13-trans prostenoic acid | dl-9a,16-dihydroxy-16-(1-fluorovinyl)-20-nor-2-homo-13-trans prostenoic acid |
| 195 | dl-16-hydroxy-9-oxo-16-(1-fluorovinyl)-2-homo-13-trans prostenoic acid | dl-9a,16-dihydroxy-16-(1-fluorovinyl)-2-homo-13-trans prostenoic acid |
| 196 | dl-16-hydroxy-9-oxo-16-(1-fluorovinyl)-20-methyl-2-homo-13-trans prostenoic acid | dl-9a,16-dihydroxy-16-(1-fluorovinyl)-20-methyl-2-homo-13-trans prostenoic acid |
| 197 | dl-16-hydroxy-9-oxo-16-(1-fluorovinyl)-20-ethyl-2-homo-13-trans prostenoic acid | dl-9a,16-dihydroxy-16-(1-fluorovinyl)-20-ethyl-2-homo-13-trans prostenoic acid |

| EXAMPLE | STARTING PROSTAGLANDIN OF THE PGE SERIES | PRODUCT PROSTAGLANDIN OF THE PGF1B SERIES |
|---|---|---|
| 198 | dl-11a,16-dihydroxy-9-oxo-16-(1-fluorovinyl)-20-nor-2-nor-13-trans prostenoic acid | dl-9B,11a,16-trihydroxy-16-(1-fluorovinyl)-20-nor-2-nor-13-trans prostenoic acid |
| 199 | dl-11a,16-dihydroxy-9-oxo-16-(1-fluorovinyl)-2-nor-13-trans prostenoic acid | dl-9B,11a,16-trihydroxy-16-(1-fluorovinyl)-2-nor-13-trans prostenoic acid |
| 200 | dl-11a,16-dihydroxy-9-oxo-16-(1-fluorovinyl)-20-methyl-2-nor-13-trans prostenoic acid | dl-9B,11a,16-trihydroxy-16-(1-fluorovinyl)-20-methyl-2-nor-13-trans prostenoic acid |
| 201 | dl-11a,16-dihydroxy-9-oxo-16-(1-fluorovinyl)-20-ethyl-2-nor-13-trans prostenoic acid | dl-9B,11a,16-trihydroxy-16-(1-fluorovinyl)-20-ethyl-2-nor-13-trans prostenoic acid |
| 202 | dl-11a,16-dihydroxy-9-oxo-16-(1-fluorovinyl)-20-nor-13-trans prostenoic acid | dl-9B,11a,16-trihydroxy-16-(1-fluorovinyl)-20-nor-13-trans prostenoic acid |
| 203 | dl-11a,16-dihydroxy-9-oxo-16-(1-fluorovinyl)-13-trans prostenoic acid | dl-9B,11a,16-trihydroxy-16-(1-fluorovinyl)-13-trans prostenoic acid |
| 204 | dl-11a,16-dihydroxy-9-oxo-16-(1-fluorovinyl)-20-methyl-13-trans prostenoic acid | dl-9B,11a,16-trihydroxy-16-(1-fluorovinyl)-20-methyl-13-trans prostenoic acid |
| 205 | dl-11a,16-dihydroxy-9-oxo-16-(1-fluorovinyl)-20-ethyl-13-trans prostenoic acid | dl-9B,11a,16-trihydroxy-16-(1-fluorovinyl)-20-ethyl-13-trans prostenoic acid |
| 206 | dl-11a,16-dihydroxy-9-oxo-16-(1-fluorovinyl)-20-nor-2-homo-13-trans prostenoic acid | dl-9B,11a,16-trihydroxy-16-(1-fluorovinyl)-20-nor-2-homo-13-trans prostenoic acid |
| 207 | dl-11a,16-dihydroxy-9-oxo-16-(1-fluorovinyl)-2-homo-13-trans prostenoic acid | dl-9B,11a,16-trihydroxy-16-(1-fluorovinyl)-2-homo-13-trans prostenoic acid |
| 208 | dl-11a,16-dihydroxy-9-oxo-16-(1-fluorovinyl)-20-methyl-2-homo-13-trans prostenoic acid | dl-9B,11a,16-trihydroxy-16-(1-fluorovinyl)-20-methyl-2-homo-13-trans prostenoic acid |
| 209 | dl-11a,16-dihydroxy-9-oxo-16-(1-fluorovinyl)-20-ethyl-2-homo-13-trans prostenoic acid | dl-9B,11a,16-trihydroxy-16-(1-fluorovinyl)-20-ethyl-2-homo-13-trans prostenoic acid |
| 210 | nat-11a,16-dihydroxy-9-oxo-16-(1-fluorovinyl)-20-nor-13-trans prostenoic acid | nat-9B,11a,16-trihydroxy-16-(1-fluorovinyl)-20-nor-13-trans prostenoic acid |
| 211 | nat-11a,16-dihydroxy-9-oxo-16-(1-fluorovinyl)-13-trans prostenoic acid | nat-9B,11a,16-trihydroxy-16-(1-fluorovinyl)-13-trans prostenoic acid |
| 212 | nat-11a,16-dihydroxy-9-oxo-16-(1-fluorovinyl)-20-methyl-13-trans prostenoic acid | nat-9B,11a,16-trihydroxy-16-(1-fluorovinyl)-20-methyl-13-trans prostenoic acid |
| 213 | nat-11a,16-dihydroxy-9-oxo-16-(1-fluorovinyl)-20-ethyl-13-trans prostenoic acid | nat-9B,11a,16-trihydroxy-16-(1-fluorovinyl)-20-ethyl-13-trans prostenoic acid |

| EXAMPLE | STARTING PROSTAGLANDIN OF THE PGE SERIES | PRODUCT PROSTAGLANDIN OF THE 11-DEOXY PGF1B SERIES |
|---|---|---|
| 214 | dl-16-hydroxy-9-oxo-16-(1-fluorovinyl)-20-nor-2-nor-13-trans prostenoic acid | dl-9B,16-dihydroxy-16-(1-fluorovinyl)-20-nor-2-nor-13-trans prostenoic acid |
| 215 | dl-16-hydroxy-9-oxo-16-(1-fluorovinyl)-2-nor-13-trans prostenoic acid | dl-9B,16-dihydroxy-16-(1-fluorovinyl)-2-nor-13-trans prostenoic acid |
| 216 | dl-16-hydroxy-9-oxo-16-(1-fluorovinyl)-20-methyl-2-nor-13-trans prostenoic acid | dl-9B,16-dihydroxy-16-(1-fluorovinyl)-20-methyl-2-nor-13-trans prostenoic acid |
| 217 | dl-16-hydroxy-9-oxo-16-(1-fluorovinyl)-20-ethyl-2-nor-13-trans prostenoic acid | dl-9B,16-dihydroxy-16-(1-fluorovinyl)-20-ethyl-2-nor-13-trans prostenoic acid |
| 218 | dl-16-hydroxy-9-oxo-16-(1-fluorovinyl)-20-nor-13-trans prostenoic acid | dl-9B,16-dihydroxy-16-(1-fluorovinyl)-20-nor-13-trans prostenoic acid |
| 219 | dl-16-hydroxy-9-oxo-16-(1-fluorovinyl)-13-trans prostenoic acid | dl-9B,16-dihydroxy-16-(1-fluorovinyl)-13-trans prostenoic acid |
| 220 | dl-16-hydroxy-9-oxo-16-(1-fluorovinyl)-20-methyl-13-trans prostenoic acid | dl-9B,16-dihydroxy-16-(1-fluorovinyl)-20-methyl-13-trans prostenoic acid |
| 221 | dl-16-hydroxy-9-oxo-16-(1-fluorovinyl)-20-ethyl-13-trans prostenoic acid | dl-9B,16-dihydroxy-16-(1-fluorovinyl)-20-ethyl-13-trans prostenoic acid |
| 222 | dl-16-hydroxy-9-oxo-16-(1-fluorovinyl)-20-nor-2-homo-13-trans prostenoic acid | dl-9B,16-dihydroxy-16-(1-fluorovinyl)-20-nor-2-homo-13-trans prostenoic acid |
| 223 | dl-16-hydroxy-9-oxo-16-(1-fluorovinyl)-2-homo-13-trans prostenoic acid | dl-9B,16-dihydroxy-16-(1-fluorovinyl)-2-homo-13-trans prostenoic acid |
| 224 | dl-16-hydroxy-9-oxo-16-(1-fluorovinyl)-20-methyl-2-homo-13-trans prostenoic acid | dl-9B,16-dihydroxy-16-(1-fluorovinyl)-20-methyl-2-homo-13-trans prostenoic acid |
| 225 | dl-16-hydroxy-9-oxo-16-(1-fluorovinyl)- | |

We claim:
1. Compounds of the formula

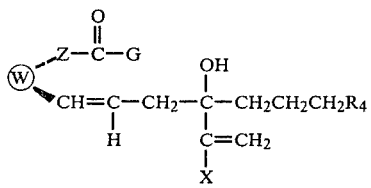

or a racemic mixture thereof and the mirror image thereof wherein W is

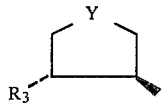

wherein
Y is

$R_3$ is selected from the group hydrogen and hydroxy; $R_4$ is selected from the group hydrogen and $C_1$ to $C_3$ alkyl; G is selected from the group hydroxy and $C_1$ to $C_6$ alkoxy; Z is selected from the group $-(CH_2)_n-$, $-(CH_2)_m OCH_2-$, and $-(CH_2)_m SCH_2-$ wherein n is the integer 5 to 8, and m is the integer 3 to 6; and X is selected from the group fluorine, chlorine and bromine and when G is hydroxy and the pharmaceutically acceptable salts thereof.

2. The compounds according to claim 1 wherein G is $-C(O)OH$ Z is $-(CH_2)_n-$ and n, X and $R_3$ are as previously defined.

3. A racemic compound according to claim 2, dl-11a,16-DIHYDROXY-9-OXO-16-(1-FLUOROVINYL)-13-trans PROSTENOIC ACID.

4. A optically active compound according to claim 2, nat-11a,16-DIHYDROXY-9-OXO-16-(1-FLUOROVINYL)-13-trans PROSTENOIC ACID.

5. A racemic compound according to claim 2, dl-11a,16a-DIHYDROXY-9-OXO-16-(1-FLUOROVINYL)-13-trans PROSTENOIC ACID.

6. A optically active compound according to claim 2, nat-11a,16a-DIHYDROXY-9-OXO-16-(1-FLUOROVINYL)-13-trans PROSTENOIC ACID.

7. A racemic compound according to claim 2, dl-11a,16B-DIHYDROXY-9-OXO-16-(1-FLUOROVINYL)-13-trans PROSTENOIC ACID.

8. A optically active compound according to claim 2, nat-11a,16B-DIHYDROXY-9-OXO-16-(1-FLUOROVINYL)-13-trans PROSTENOIC ACID.

9. A racemic compound according to claim 2, dl-11a,16-DIHYDROXY-9-OXO-16-(1-FLUOROVINYL)-13-trans PROSTENOIC ACID METHYL ESTER.

10. A optically active compound according to claim 2, nat-11a,16-DIHYDROXY-9-OXO-16-(1-FLUOROVINYL)-13-trans PROSTENOIC ACID METHYL ESTER.

11. A racemic compound according to claim 2, dl-11a,16a-DIHYDROXY-9-OXO-16-(1-FLUOROVINYL)-13-trans PROSTENOIC ACID METHYL ESTER.

12. A optically active compound according to claim 2, nat-11a,16a-DIHYDROXY-9-OXO-16-(1-FLUOROVINYL)-13-trans PROSTENOIC ACID METHYL ESTER.

13. A racemic compound according to claim 2, dl-11a,16P-DIHYDROXY-9-OXO-16-(1-FLUOROVINYL)-13-trans PROSTENOIC ACID METHYL ESTER.

14. A optically active compound according to claim 2, nat-11a,16B-DIHYDROXY-9-OXO-16-(1-FLUOROVINYL)-13-trans PROSTENOIC ACID METHYL ESTER.

15. A racemic compound according to claim 2, dl-16-HYDROXY-9-OXO-16-(1-FLUOROVINYL)-13-trans PROSTENOIC ACID.

16. A racemic compound according to claim 2, dl-16a-HYDROXY-9-OXO-16-(1-FLUOROVINYL)-13-trans PROSTENOIC ACID.

17. A racemic compound according to claim 2, dl-16B-HYDROXY-9-OXO-16-(1-FLUOROVINYL)-13-trans PROSTENOIC ACID.

18. A racemic compound according to claim 2, dl-16-HYDROXY-9-OXO-16-(1-FLUOROVINYL)-13-trans PROSTENOIC ACID METHYL ESTER.

19. A racemic compound according to claim 2, dl-16a-HYDROXY-9-OXO-16-(1-FLUOROVINYL)-13-trans PROSTENOIC ACID METHYL ESTER.

20. A racemic compound according to claim 2, dl-16B-HYDROXY-9-OXO-16-(1-FLUOROVINYL)-13-trans PROSTENOIC ACID METHYL ESTER.

* * * * *